US010561356B2

(12) United States Patent
Nakahata et al.

(10) Patent No.: US 10,561,356 B2
(45) Date of Patent: Feb. 18, 2020

(54) DRIVER'S PHYSICAL CONDITION DETECTION DEVICE AND METHOD

(71) Applicant: MAZDA MOTOR CORPORATION, Hiroshima (JP)

(72) Inventors: Youichiro Nakahata, Aki-gun (JP); Yohei Iwashita, Hiroshima (JP); Junichiro Kuwahara, Hiroshima (JP); Ryohei Hisamitsu, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 84 days.

(21) Appl. No.: 15/683,193

(22) Filed: Aug. 22, 2017

(65) Prior Publication Data

US 2018/0055438 A1  Mar. 1, 2018

(30) Foreign Application Priority Data

Aug. 26, 2016 (JP) .................................. 2016-166124

(51) Int. Cl.
*A61B 5/18* (2006.01)
*A61B 5/11* (2006.01)
(Continued)

(52) U.S. Cl.
CPC .............. *A61B 5/18* (2013.01); *A61B 5/1114* (2013.01); *A61B 5/1128* (2013.01); *A61B 5/72* (2013.01);
(Continued)

(58) Field of Classification Search
CPC ....... A61B 5/18; A61B 5/1114; A61B 5/1128; A61B 5/72; B60K 28/02; B60W 2040/0818
See application file for complete search history.

(56) References Cited

U.S. PATENT DOCUMENTS 7,164,117 B2 * 1/2007 Breed ............... B60R 21/01516
250/208.1
7,389,171 B2 * 6/2008 Rupp ................. B60K 31/0008
180/170
(Continued)

FOREIGN PATENT DOCUMENTS

JP  2007-524134 A  8/2007
JP  2011-123653 A  6/2011
(Continued)

OTHER PUBLICATIONS

An Office Action issued by the Japanese Patent Office dated Dec. 5, 2017, which corresponds to Japanese Patent Application No. 2016-166124 and is related to U.S. Appl. No. 15/683,193; with English language concise explanation.

*Primary Examiner* — Behrang Badii
*Assistant Examiner* — Daniel L Greene
(74) *Attorney, Agent, or Firm* — Studebaker & Brackett PC

(57) ABSTRACT

A driver's physical condition detection device for detecting a physical condition of a driver driving a vehicle, includes: a vehicle detector configured to detect a change in motion of the vehicle during driving; a driver detector configured to detect a change in motion of the driver; a calculator configured to calculate a follow-up degree of the change in motion of the driver with respect to the change in motion of the vehicle during driving; and a physical condition determination portion configured to perform a determination process of determining whether or not the physical condition of the driver is deteriorated, based on the follow-up degree.

4 Claims, 19 Drawing Sheets

(51) Int. Cl.
*A61B 5/00* (2006.01)
*B60K 28/02* (2006.01)
*B60W 40/08* (2012.01)

(52) U.S. Cl.
CPC ...... *B60K 28/02* (2013.01); *B60W 2040/0818* (2013.01)

(56) References Cited

U.S. PATENT DOCUMENTS

| | | | |
|---|---|---|---|
| 7,423,540 B2 * | 9/2008 | Kisacanin | G06K 9/00362 340/576 |
| 9,409,517 B2 * | 8/2016 | Han | B60Q 9/00 |
| 2003/0209893 A1 * | 11/2003 | Breed | B60J 10/00 280/735 |
| 2006/0232430 A1 | 10/2006 | Takaoka et al. | |
| 2007/0008151 A1 * | 1/2007 | Victor | A61B 5/11 340/573.1 |
| 2007/0228703 A1 * | 10/2007 | Breed | B60N 2/0232 280/735 |
| 2012/0323479 A1 * | 12/2012 | Nagata | B60Q 9/008 701/301 |
| 2016/0001781 A1 * | 1/2016 | Fung | B60W 40/08 701/36 |

FOREIGN PATENT DOCUMENTS

| | | |
|---|---|---|
| JP | 2013-069184 A | 4/2013 |
| JP | 2015-021912 A | 2/2015 |
| JP | 2016-009257 A | 1/2016 |
| JP | 2016-088497 A | 5/2016 |
| WO | 2004/082479 A1 | 9/2004 |

\* cited by examiner

DRIVER'S PHYSICAL CONDITION DETECTION DEVICE AND METHOD

TECHNICAL FIELD

The technique disclosed herein relates to a driver's physical condition detection device and method for detecting a physical condition of a driver.

BACKGROUND ART

As one of the causes of death by traffic accident, there is a sudden change in the physical condition of a driver during driving. A cause of a sudden change in the driver's physical condition includes various diseases such as cerebrovascular diseases and heart diseases. The condition of a driver who cannot continue driving by a sudden change in the physical condition is not constant. Conventionally, there is known a technique for detecting a sudden change in the driver's physical condition (see e.g. Japanese Unexamined Patent Publication No. 2015-021912). In the technique described in Japanese Unexamined Patent Publication No. 2015-021912, a deteriorated physical condition of a driver is estimated based on a driving position of the driver to detect a sign of deterioration of the physical condition.

Generally, it is often the case that by the time when a large change in the driving position of a driver appears. a deteriorated physical condition of the driver progresses to a certain extent. In order to secure safety of a driver, however, it is necessary to detect a deteriorated physical condition of the driver at an early stage before the deteriorated physical condition progresses.

SUMMARY OF THE INVENTION

The technique disclosed herein is directed to detecting a deteriorated physical condition of a driver at an early stage before the deteriorated physical condition progresses.

An aspect of the technique disclosed herein is directed to a driver's physical condition detection device for detecting a physical condition of a driver driving a vehicle. The driver's physical condition detection device includes a vehicle detector configured to detect a change in motion of the vehicle during driving; a driver detector configured to detect a change in motion of the driver; a calculator configured to calculate a follow-up degree of the change in motion of the driver with respect to the change in motion of the vehicle during driving; and a physical condition determination portion configured to perform a determination process of determining whether or not the physical condition of the driver is deteriorated, based on the follow-up degree.

According to an aspect of the present disclosure, the determination process of determining whether or not the driver's physical condition is deteriorated is performed, based on the follow-up degree of the change in motion of the driver with respect to the change in motion of the vehicle during driving. Therefore, it is possible to detect a deteriorated physical condition of a driver at an early stage before the deteriorated physical condition of the driver progresses.

These and other objects, features and advantages of the present invention will become more apparent upon reading the following detailed description along with the accompanying drawings.

Figure 1:
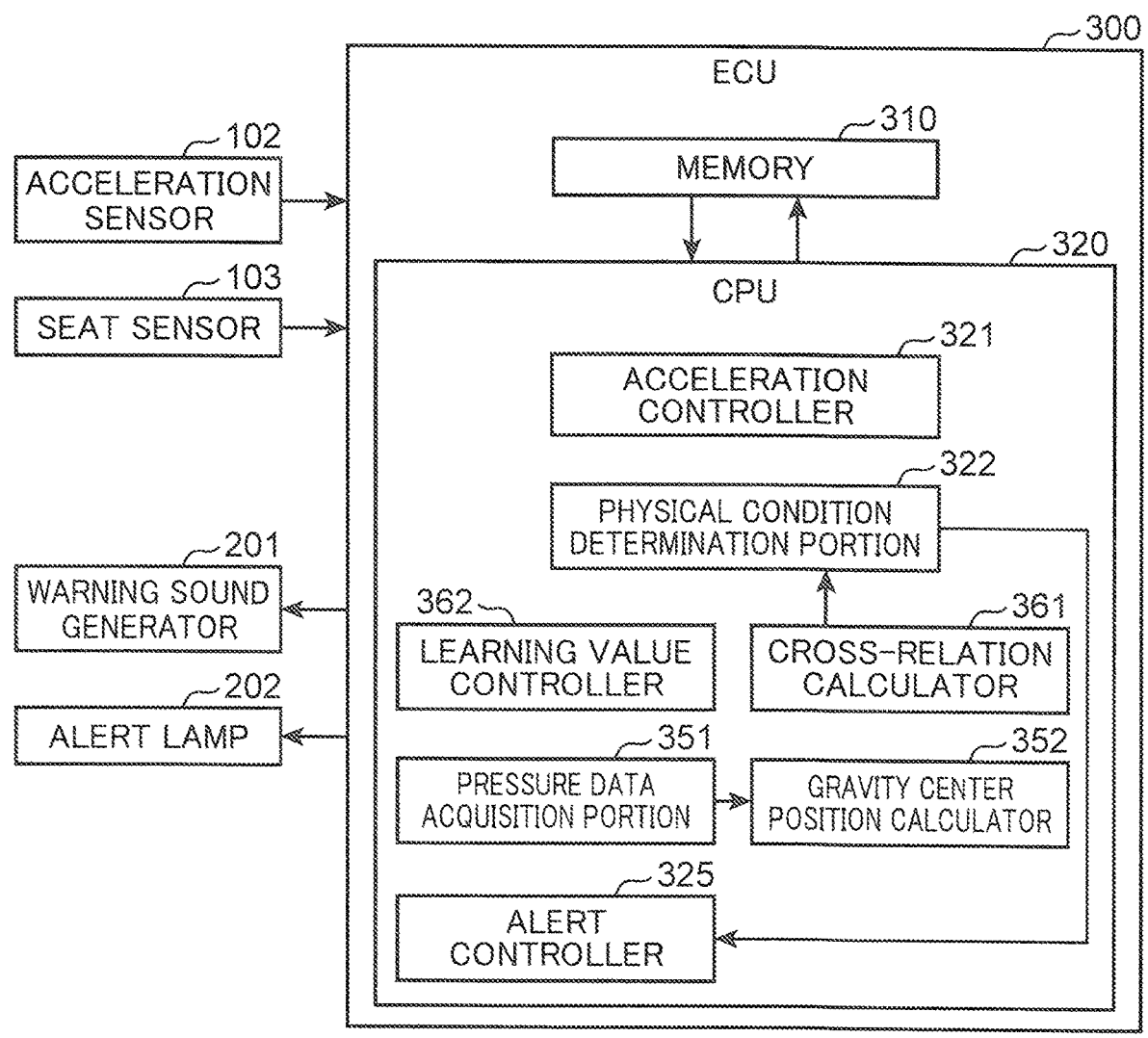
FIG. 1 is a block diagram schematically illustrating a configuration of a vehicle, in which a drivers physical condition detection device of a first embodiment is mounted.

DESCRIPTION OF EMBODIMENTS (Outline of Aspect of Present Disclosure)

First of all, an outline of an aspect of the present disclosure is described. As a result of conducting various experiments, the inventors of the present application found that there is a difference in a follow-up degree of a change of motion of a driver with respect to a change in motion of a vehicle between a case where a driver's physical condition is normal, and a case where a driver's physical condition is deteriorated.

Specifically, when motion of a vehicle changes, motion of a driver also changes to follow up the change in motion of the vehicle. Since the change in motion of the driver is in response to the change in motion of the vehicle, the change in motion of the driver delays with respect to the change in motion of the vehicle. The above-described "follow-up degree" represents a degree of delay of the change in motion of the driver with respect to the change in motion of the vehicle.

Regarding the aforementioned difference in the follow-up degree, the inventors assume as follows. Specifically, a driver whose physical condition is normal predicts that an acceleration of a vehicle in a left-right direction of the vehicle may be exerted from the vehicle when the vehicle enters a curve from a straight road. Then, the driver tries to resist against the acceleration in the left-right direction, which may be exerted from the vehicle, with use of the muscles of the neck or the upper body. As a result, a follow-up degree of the change in motion of the driver with respect to the change in motion of the vehicle may be lowered.

On the other hand, when a driver's physical condition is deteriorated, the muscles of the neck may be weakened particularly, due to slight lowering of the consciousness. As a result, the muscles of the upper body may be weakened. Then, the follow-up degree of the change in motion of the driver with respect to the change in motion of the vehicle may increase. In this example, "a left-right direction of a vehicle" is a direction orthogonal to a front-rear direction of the vehicle within a horizontal plane. In other words, "a left-right direction of a vehicle" is a direction orthogonal to a traveling direction of the vehicle travelling on a straight road within a horizontal plane. "A left-right direction of a vehicle" may also be referred to as "a vehicle width direction" or "a vehicle transverse direction".

Note that in the following, an experiment was conducted by letting a subject be seated on a front passenger seat in a state that the visual and audible sensations were deprived of in order to simulate a driver whose physical condition is deteriorated. The subject cannot predict that an acceleration in the left-right direction may be exerted from the vehicle when the vehicle enters a curve, because the subject's visual and audible sensations are deprived of. As a result, it may be difficult for the subject to resist against the acceleration in the left-right direction, which may be exerted from the vehicle, with use of the muscles of the neck or the upper body. In this way, a driver whose physical condition is deteriorated, and whose muscles of the neck or the upper body are weakened, is simulated.

In view of the aforementioned observation, the inventors found that it is possible to detect a deteriorated physical condition of a driver at an early stage by checking a follow-tip degree of a change in motion of a driver with respect to a change in motion of a vehicle.

(Embodiments)

In the following, embodiments of the present disclosure are described with reference to the drawings. Note that in the drawings, same constituent elements are indicated by the same reference numerals, and repeated description thereof is omitted as necessary.

(First Embodiment)

FIG. 1 is a block diagram schematically illustrating a configuration of a vehicle. in which a driver's physical condition detection device of the first embodiment is mounted. A vehicle 10 is a four wheel vehicle, for instance. As illustrated in FIG. 1, the vehicle 10 includes a camera 101, an acceleration sensor 102, a seat sensor 103, a warning sound generator 201, an alert lamp 202, and an electronic control unit (ECU) 300.

The acceleration sensor 102 (an example of the vehicle detector) detects an acceleration of the vehicle 10 in three axes directions perpendicular to each other, for instance. The acceleration sensor 102 outputs a detected acceleration of the vehicle 10 to the ECU 300. The seat sensor 103 (an example of the driver detector) is disposed on a seat surface portion of a driver's seat. The seat sensor 103 includes 32×32 piezoelectric elements, for instance, and detects a pressure distribution of a driver seated on the driver's seat. The seat sensor 103 outputs detection data to the ECU 300.

The warning sound generator 201 includes an electronic buzzer, for instance, and generates a warning sound to the driver. The alert lamp 202 includes a light emitting diode, for instance, and displays an alert to the driver. Note that the alert lamp 202 is not limited to a dedicated lamp, and may also be used as an alert lamp by causing a meter on an instrument panel or the like to blink.

The ECU 300 controls the overall operation of the vehicle 10. The ECU 300 includes a memory 310, a central processing unit (CPU) 320, and peripheral circuits. The memory 310 is constituted by a semiconductor memory such as a flash memory, a hard disk, or another storage element, for instance. The memory 310 includes a memory configured to store a program, and a memory configured to temporarily store data. The memory 310 may he constituted by a single memory having an area for storing a program, and an area for temporarily storing data.

The CPU 320 functions as an acceleration controller 321, a physical condition determination portion 322, an alert controller 325, a pressure data acquisition portion 351, a gravity-center-position calculator 352, a cross-correlation calculator 361, and a learning value controller 362 by being operated in accordance with a program stored in the memory 310.

The acceleration controller 321 acquires an acceleration of the vehicle 10 in a left-right direction of the vehicle 10 from acceleration data of the vehicle 10 in three axes directions perpendicular to each other, for instance, which is output from the acceleration sensor 102 every predetermined period (e.g. every 100 msec.). The acceleration controller 321 stores time data of an acceleration of the vehicle 10 in the left-right direction, which is obtained for a predetermined period (in the embodiment, e.g. for ten seconds) in the memory 310. When the predetermined period is ten seconds, for instance, and acceleration data is acquired from the acceleration sensor 102 every 100 msec., one hundred pieces of time data of acceleration are stored in the memory 310.

The pressure data acquisition portion 351 acquires pressure data on each piezoelectric element to be output from the seat sensor 103. The pressure data acquisition portion 351 outputs acquired pressure data to the gravity-center-position calculator 352. The gravity-center-position calculator 352 calculates a gravity-center-position of the driver in a left-right direction of the vehicle 10 with use of pressure data from the pressure data acquisition portion 351. The gravity-center-position calculator 352 stores data of the gravity-center-position of the driver for a predetermined period in the memory 310. In the embodiment, the predetermined period is ten seconds, for instance.

Figure 2:
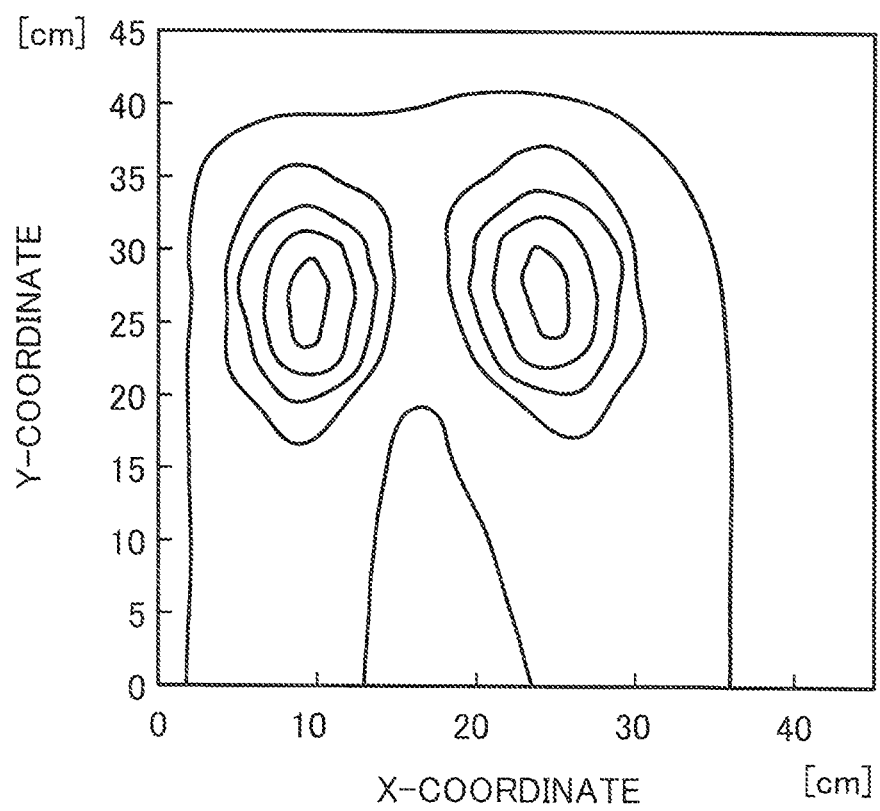
FIG. 2 is a diagram schematically illustrating an example of a pressure distribution of a driver seated on a driver's seat, which is detected by a seat sensor.

FIG. 2 is a diagram schematically illustrating an example of a pressure distribution of a driver seated on the driver's seat, which is detected by the seat sensor 103. FIG. 2 illustrates equal-pressure lines, each of which has a same pressure value. In FIG. 2, a pressure value at a center position of an area where the equal-pressure lines are densely distributed has a highest pressure value.

The seat sensor 103 outputs a set of coordinates and a pressure value of each piezoelectric element to the ECU 300 as serial data, for instance. The pressure data acquisition portion 351 applies a process to received serial data, and outputs a set of coordinates and a pressure value of each piezoelectric element to the gravity-center-position calculator 352. The gravity-center-position calculator 352 calculates a position of a gravity center of the driver in the left-right direction (in an X-axis direction in FIG. 2) of the vehicle 10 from a set of coordinates and a pressure value of each piezoelectric element. The gravity-center-position calculator 352 calculates a position of a gravity center of the driver, as a distance from the origin point in the X-axis for instance.

Referring back to FIG. 1, the cross-correlation calculator 361 (an example of the calculator) calculates a cross-correlation between time data of an acceleration of the vehicle 10 in the left-right direction, which is stored in the memory 310 by the acceleration controller 321, and time data of a gravity-center-position of the driver, which is stored in the memory 310 by the gravity-center-position calculator 352. A cross-correlation is obtained by convoluting one of two functions by reversing the order of a signal array with use of a convolution formula of convoluting the two functions. In the embodiment, the two functions are a function representing time data of an acceleration of the vehicle 10 in the left-right direction, and a function representing time data of a gravity-center-position of the driver. The cross-correlation calculator 361 calculates a time delay from an obtained cross-correlation.

Figure 3A:
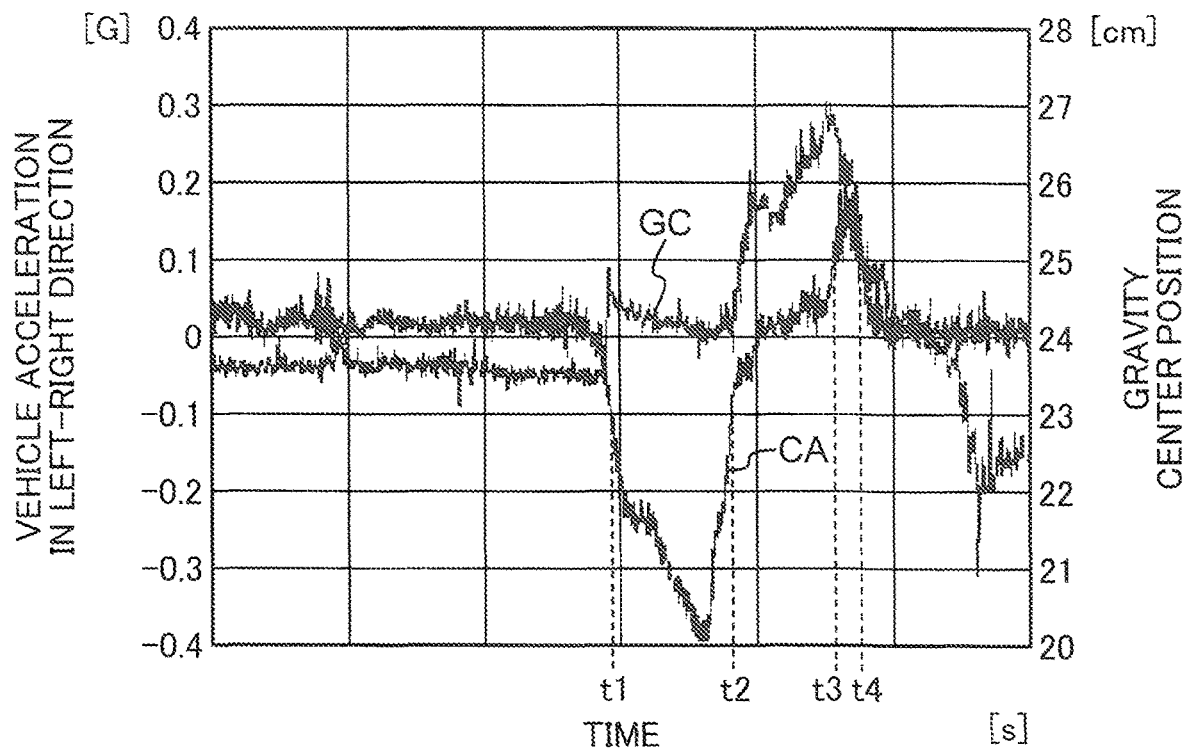
FIG. 3A is a diagram schematically illustrating an example of time data of an acceleration of a vehicle in a left-right direction of the vehicle and time data of a gravity-center-position of a driver stored in a memory by a gravity center-position calculator.
Figure 3B:
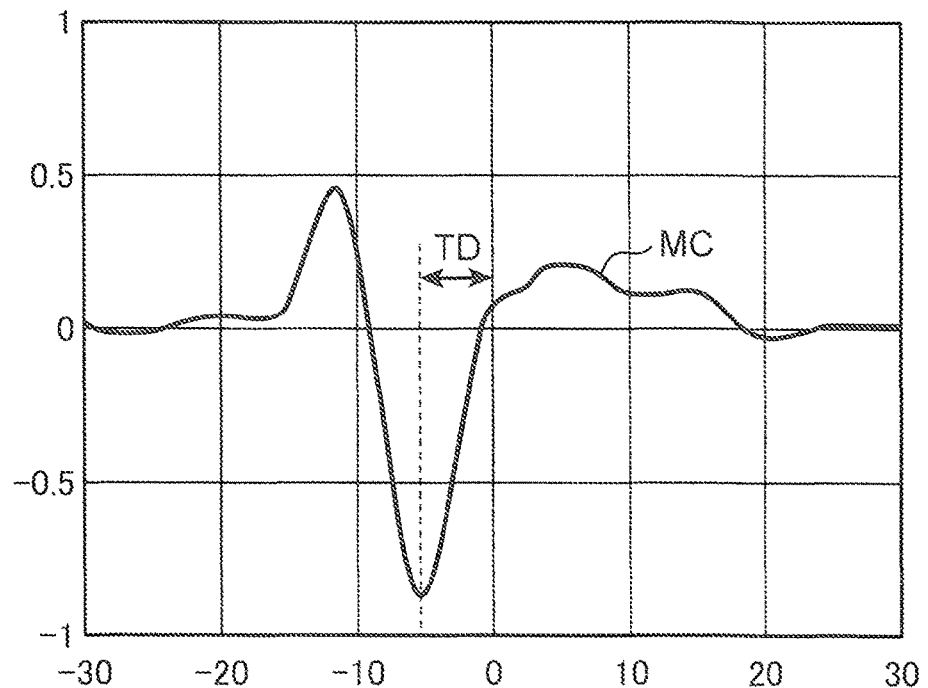
FIG. 3B is a diagram schematically illustrating an example of a cross-correlation between the pieces of time data shown in FIG. 3A.
Figure 4A:
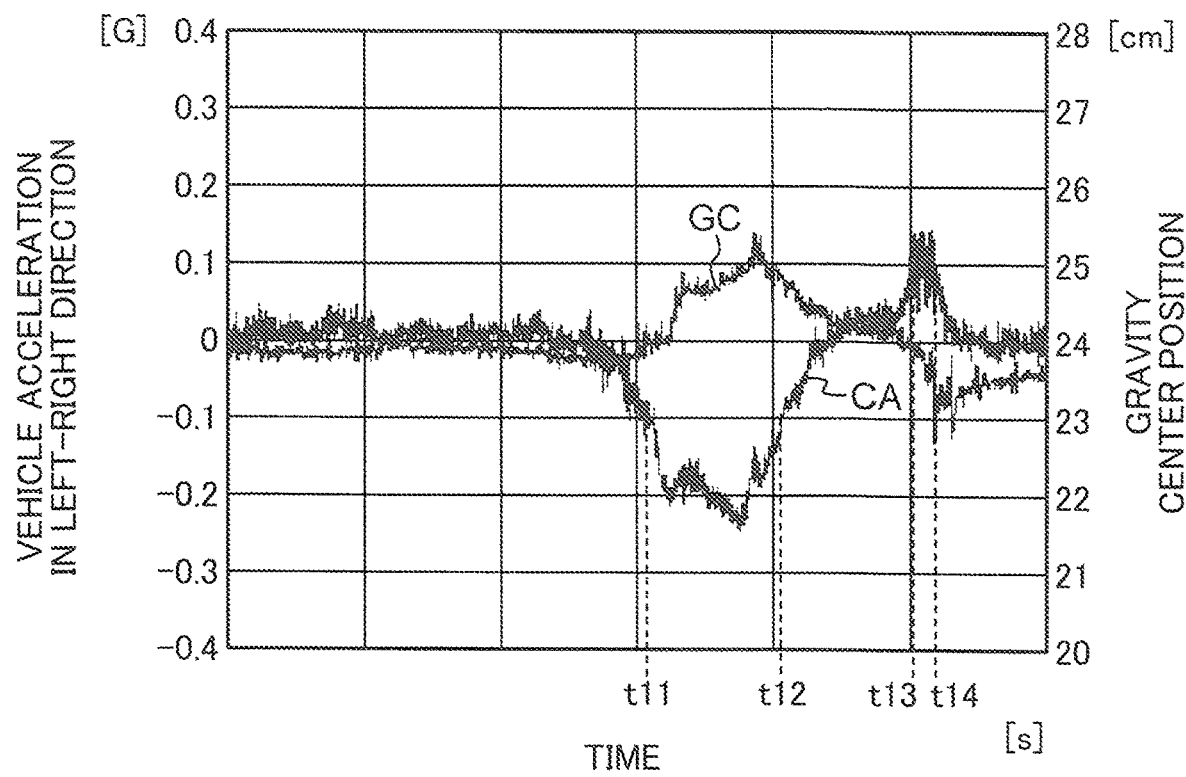
FIG. 4A is a diagram schematically illustrating an example of time data of an acceleration of a vehicle in a left-right direction of the vehicle and time data of a gravity-center-position of a driver stored in the memory by the gravity-center-position calculator.

FIG. 3A, FIG. 3B, FIG. 4A, and FIG. 4B are diagrams schematically illustrating an example of time data of an acceleration of the vehicle 10 in the left-right direction, time data of a gravity-center-position of the driver, which is stored in the memory 310 by the gravity-center-position calculator 352, and a cross-correlation between these pieces of time data. FIG. 3A and FIG. 4A denote time data of an acceleration CA of the vehicle 10 in the left-right direction. and time data of the gravity-center-position GC of the driver in the left-right direction. In FIG. 3A and FIG. 4A, the horizontal axis denotes a time [second], the left vertical axis denotes an acceleration [G], and the right vertical axis denotes a gravity-center-position [cm]. FIG. 3A indicates a case where a driver's physical condition is normal, and FIG. 4A indicates a case where a driver's physical condition is deteriorated.

Figure 4B:
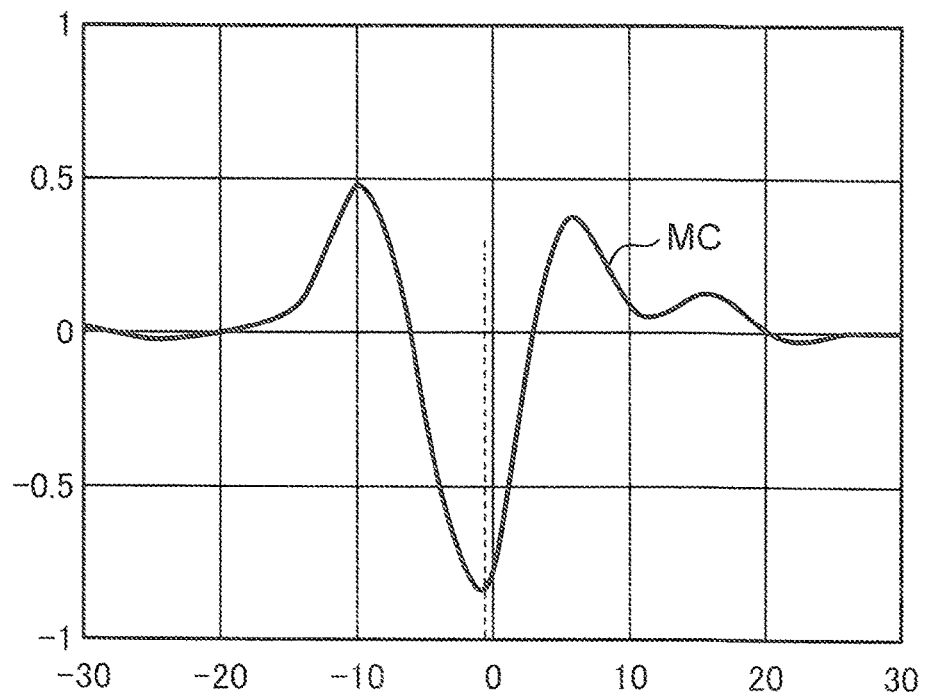
FIG. 4B is a diagram schematically illustrating an example of a cross-correlation between the pieces of time data shown in FIG. 4A.

FIG. 3B and FIG. 4B respectively indicate a cross-correlation MC between time data of the acceleration CA, and time data of the gravity-center-position GC illustrated in FIG. 3A and FIG. 4A. In FIG. 3B and FIG. 4B, the horizontal axis denotes a time delay, and the vertical axis denotes a magnitude of a correlation value.

FIG. 3B illustrates that there is a negative correlation because the peak value of a correlation value is near (−1), and there is a time delay TD because the peak value of the correlation value is deviated from a time delay "0". FIG. 4B illustrates that there is a negative correlation because the peak value of the correlation value is near (−1), and there is no time delay because the time delay "0" and the peak value of the correlation value coincide with each other.

As illustrated in FIG. 3A and FIG. 4A, an acceleration of the vehicle 10 in the left-right direction increases, since the vehicle 10 travelling on a straight road enters a curve. In response to this increase of the acceleration, the gravity-center-position of the driver in the left-right direction moves. When an acceleration of the vehicle 10 in the left-right direction increases, the driver whose physical condition is normal tries to tighten the muscles of the upper body and tries to secure good visibility so that the visibility is not impaired by the increase in the acceleration. As a result, as illustrated in FIG. 3B, there is a time delay TD in the cross-correlation MC between time data of the acceleration CA and time data of the gravity-center-position GC. In other words, the follow-up degree of a change in motion of the driver with respect to a change in motion of the vehicle 10 during driving is low.

On the other hand, it is difficult for the driver whose physical condition is deteriorated to tighten the muscles of the upper body, when an acceleration of the vehicle 10 in the left-right direction increases. As a result, the gravity-center-position of the driver moves, in response to the increase of the acceleration. Consequently, as illustrated in FIG. 4B, there is hardly any time delay between time data of the acceleration CA, and time data of the gravity-center-position GC. In other words, the follow-up degree of a change in motion of the driver with respect to a change in motion of the vehicle 10 during driving is high.

Referring back to FIG. 1, the learning value controller 362 regards that a driver's physical condition is normal during a period until a predetermined time elapses after an ignition switch of the vehicle 10 is turned on, and stores, in the memory 310, an average value of a time delay in a cross-correlation between time data of the acceleration CA and time data of the gravity-center-position GC, which are obtained during the predetermined period, as a learned value.

The physical condition determination portion 322 compares a time delay in a cross-correlation between time data of the acceleration CA of the vehicle 10 in the left-right direction and time data of the gravity-center-position GC of the driver, with the learned value stored in the memory 310, and determines whether or not a driver's physical condition is deteriorated based on the comparison result. Specifically, the physical condition determination portion 322 determines that the driver's physical condition is deteriorated when a time delay in the cross-correlation between time data of the acceleration CA and time data of the gravity-center-position GC is not more than a value K1 times as large as the learned value. The coefficient K1 is a value smaller than 1. In the embodiment, K1×0.5, for instance. The physical condition determination portion 322 notifies the alert controller 325 that the driver's physical condition is deteriorated when the physical condition determination portion 322 determines that the driver's physical condition is deteriorated.

The physical condition determination portion 322 determines whether or not a driver's physical condition is deteriorated only when an acceleration of the vehicle 10 in the left-right direction is not less than a predetermined acceleration threshold value ACth. This is because as far as the acceleration of the vehicle 10 in the left-right direction is small, there is no significant difference, in a time delay in a cross-correlation between time data of the acceleration CA and time data of the gravity-center-position GC, between a case where a driver's physical condition is normal and a case where a driver's physical condition is deteriorated. In the embodiment, ACth=0.1 [G] for instance.

When the alert controller 325 is notified that the driver's physical condition is deteriorated from the physical condition determination portion 322, the alert controller 325 activates the warning sound generator 201 and causes the alert lamp 202 to blink, to alert the driver. The alert controller 325 may activate a brake to decelerate or stop the vehicle 10, or may control a steering wheel to move the vehicle 10 to the edge of a road for instance, so as to support driving by the driver.

Figure 5:
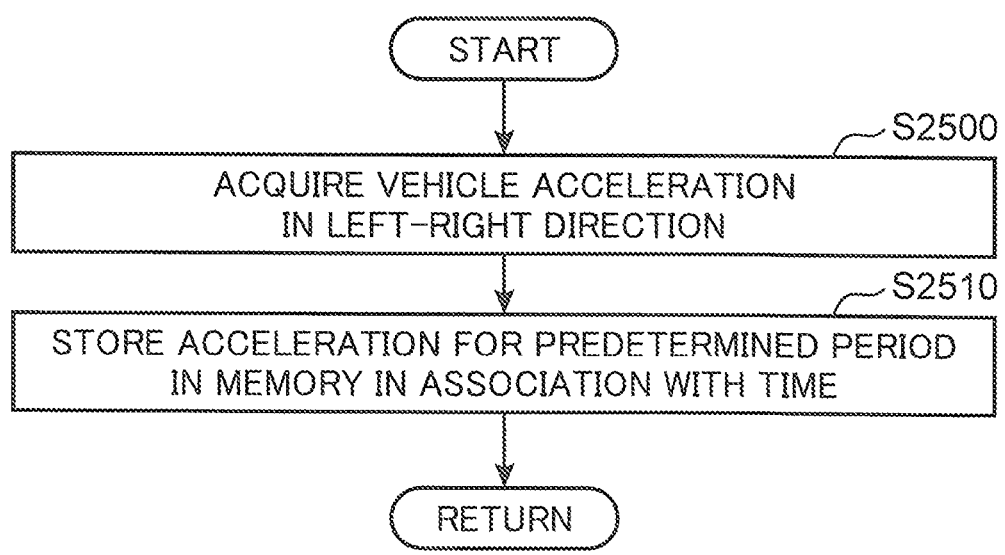
FIG. 5 is a flowchart schematically illustrating an example of a procedure of acquiring an acceleration of a vehicle in the driver's physical condition detection device of the first embodiment.

FIG. 5 is a flowchart schematically illustrating an example of a procedure of acquiring, an acceleration of a vehicle in the driver's physical condition detection device of the first embodiment. The flow illustrated in FIG. 5 is executed every predetermined period (e.g. every 100 msec.). In step S2500, the acceleration controller 321 acquires an acceleration of the vehicle 10 in the left-right direction from acceleration data of the vehicle 10 in three axes directions orthogonal to each other, for instance, which is output from the acceleration sensor 102. In step S2510, the acceleration controller 321 stores time data of acceleration of the vehicle 10 in the left-right direction for a predetermined period (in the embodiment, e.g. for ten seconds) in the memory 310. In other words, the acceleration controller 321 erases oldest acceleration data from the memory 310 when new acceleration data is obtained so that acceleration data for a predetermined period is stored in the memory 310. Thereafter, the process of FIG. 5 is terminated.

Figure 6:
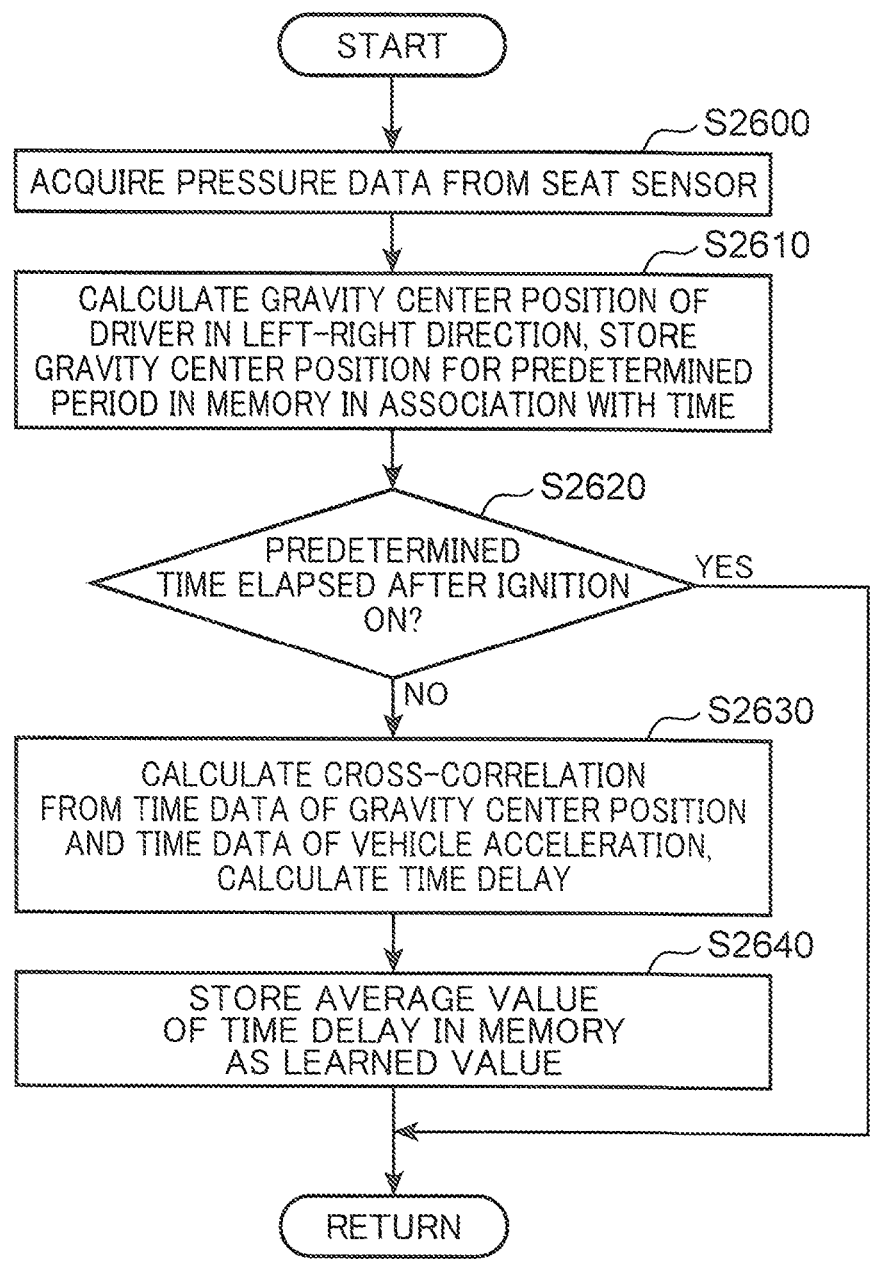
FIG. 6 is a flowchart schematically illustrating an example of a procedure of calculating a learned value of a time delay in the driver's physical condition detection device of the first embodiment.

FIG. 6 is a flowchart schematically illustrating an example of a procedure of calculating a learned value of a time delay in the driver's physical condition detection device of the first embodiment. The flow illustrated in FIG. 6 is executed every predetermined period (e.g. every 100 msec.).

In step S2600, the pressure data acquisition portion 351 acquires pressure data from the seat sensor 103. In step S2610, the gravity-center-position calculator 352 calculates a gravity-center-position of the driver in the left-right direction. The gravity-center-position calculator 352 stores time data of the gravity-center-position of the driver for a predetermined period in the memory 310.

In step S2620, the learning value controller 362 determines whether or not a predetermined period elapses after the ignition switch of the vehicle 10 is turned on.

When a predetermined period does not elapse after the ignition switch of the vehicle 10 is turned on (NO in step S2620), the process proceeds to step S2630. On the other hand, when a predetermined period elapses after the ignition switch of the vehicle 10 is turned on (YES in step S2620), the process of FIG. 6 is terminated. Specifically, when a judgement result, in step S2620 is NO, it is judged that the driver's physical condition is normal, and the process proceeds to step S2630 to perform a step of obtaining the learned value. On the other hand, when a judgment result in step S2620 is YES, the process of FIG. 6 is terminated without performing a process of obtaining the learned value.

In step S2630, the cross-correlation calculator 361 calculates a cross-correlation from time data of a gravity-center-position and time data of an acceleration of the vehicle, which are stored in the memory 310, and calculates a time delay of a peak value of a correlation value. In step S2640, the learning value controller 362 stores an average value of the calculated time delay in the memory 310, as a learned value. Thereafter, the process of FIG. 6 is terminated.

Figure 7:
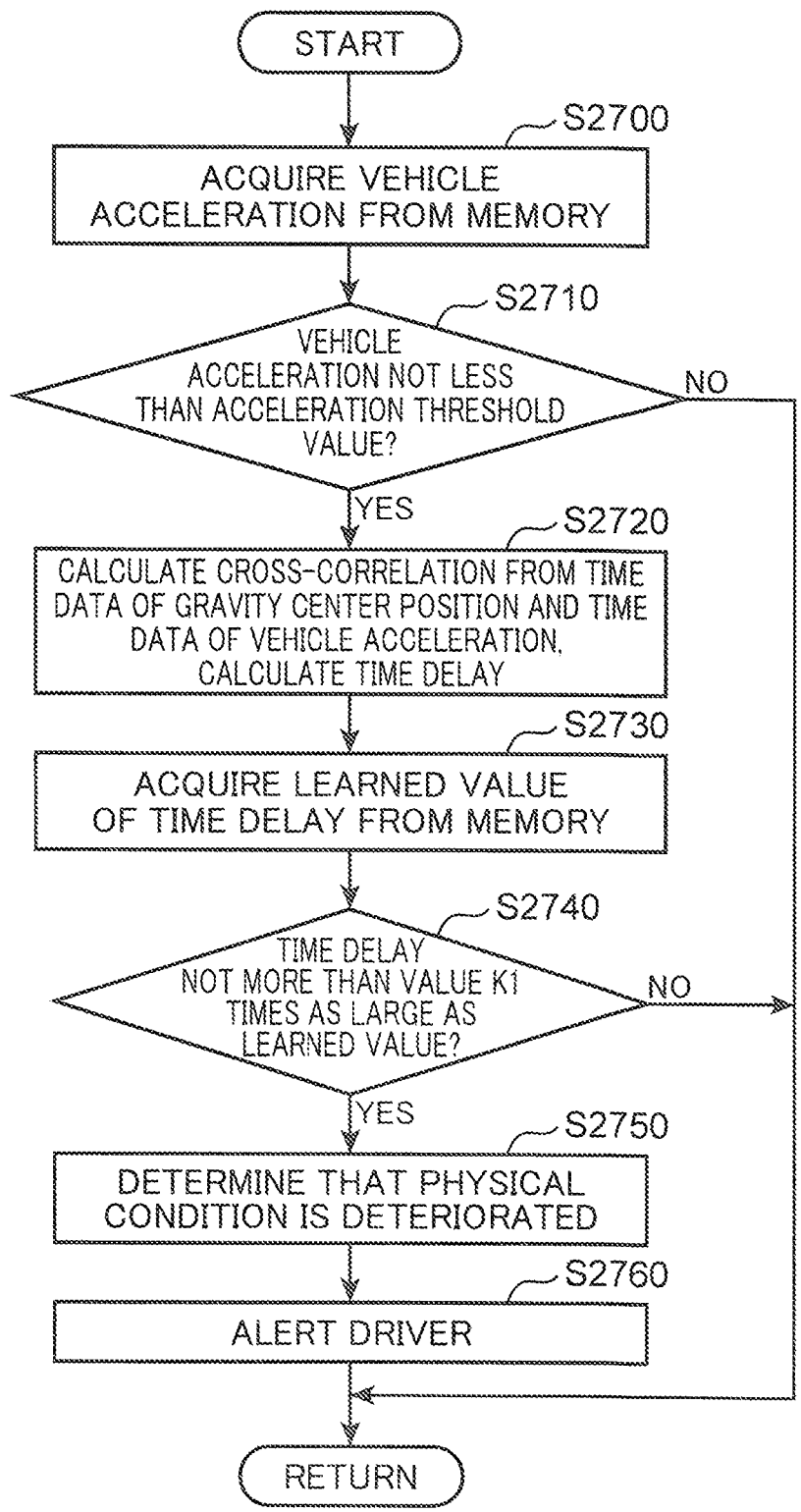
FIG. 7 is a flowchart schematically illustrating an example of a procedure of determining a driver's physical condition in the driver's physical condition detection device of the first embodiment.

FIG. 7 is a flowchart schematically illustrating an example of a procedure of determining a driver's physical condition in the driver's physical condition detection device of the first embodiment. The flow illustrated in FIG. 7 is executed every predetermined period (e.g. every 100 msec.).

In step S2700, the physical condition determination portion 322 acquires a latest acceleration CAn out of time data of acceleration of the vehicle 10 in the left-right direction, which is stored in the memory 310 (in the embodiment, e.g. data acquired for 10 seconds). In step S2710, the physical condition determination portion 322 determines whether or not the absolute value of the acquired latest acceleration CAn of the vehicle in the left-right direction is not less than the acceleration threshold value ACth. When the absolute value of the latest acceleration CAn of the vehicle in the left-right direction is less than the acceleration threshold value ACth (No n step S2710), the process of FIG. 7 is terminated. On the other hand, when the absolute value of the latest acceleration CAn of the vehicle in the left-right direction is not less than the acceleration threshold value ACth (YES in step S2710), the process proceeds to step S2720.

As described above, in the embodiment, ACth=0.1 [G], for instance. Further, for instance, in FIG. 3A, the time t1 is a point of time when the absolute value of the acceleration CA of a vehicle in, the left-right direction is not less than 0.1 [G]. The time t2 is a point of time when the absolute value of the acceleration CA of the vehicle in the left-right direction is less than 0.1 [G] after the time t1. The time t3 is a point of time when the absolute value of the acceleration CA of the vehicle in the left-right direction is not less than 0.1 [G] after the time t2. The time t4 is a point of time when the absolute value of the acceleration CA of the vehicle in the left-right direction is less than 0.1 [G] after the time t3.

Therefore, in FIG. 3A for instance, during a period from a measurement start time to the time t1, a judgment result in step S2710 is NO, and the process of FIG. 7 is terminated. Thereafter, during a period from the time t1 to the time t2, and during a period from the time t3 to the time t4, a judgement result in step S2710 is YES, and the process proceeds to step S2720.

Furthermore, in FIG. 4A for instance, the time t11 is a point of time when the absolute value of the acceleration CA of the vehicle in the left-right direction becomes not less than 0.1 [G]. The time t12 is a point of time when the absolute value of the acceleration CA of the vehicle in the left-right direction becomes less than 0.1 [G] after the time t11. The time t13 is a point of time when the absolute value of the acceleration CA of the vehicle in the left-right direction becomes not less than 0.1 [G] after the time t12. The time t14 is a point of time when the absolute value of the acceleration CA of the vehicle in the left-right direction becomes less than 0.1 [G] after the time t13.

Therefore, in FIG. 4A for instance, during a period from a measurement start time to the time t11, a judgment result in step S2710 is NO, and the process of FIG. 7 is terminated. Thereafter, during a period from the time t11 to the time t12, and during a period from the time t13 to the time t14, a judgement result in step S2710 is YES, and the process proceeds to step S2720.

Referring back to FIG. 7, in step S2720, the cross-correlation calculator 361 calculates a cross-correlation between time data of a gravity-center-position. and time data of an acceleration of the vehicle; and calculates a time delay of a peak value of a correlation value. In step S2730, the physical condition determination portion 322 acquires the learned value of a time delay stored in the memory 310, from the memory 310.

In step S2740, the physical condition determination portion 322 determines whether or not the time delay calculated in step S2720 is not more than a value K1 times as large as the learned value acquired in step S2730. When the calculated time delay is more than a value K1 times as large as the learned value (NO in step S2740), the process of FIG. 7 is terminated. When the calculated time delay is not more than a value K1 times as large the learned value (YES in step S2740), the process proceeds to step S2750.

In step S2750, the physical condition determination portion 322 determines that the driver's physical condition is deteriorated, and notifies the alert controller 325 that the driver's physical condition is deteriorated. In step S2760, the alert controller 325 activates the warning sound generator 201 and the alert lamp 202 to notify that the driver's physical condition is deteriorated. Thereafter, the process of FIG. 7 is terminated.

As described above, in the first embodiment, the cross-correlation calculator 361 calculates a cross-correlation from time data of a gravity-center-position and time data of an acceleration of the vehicle, and calculates a time delay of a peak value of a correlation value. The physical condition determination portion 322 determines that the driver's physical condition is deteriorated when the time delay is not more than the value K1 times as large as the learned value. When a driver's physical condition is deteriorated, the muscles of the neck or the upper body may be weakened due to slight lowering of the consciousness, and it may be difficult for the driver to tighten the muscles of the upper body. As a result, as an acceleration of the vehicle 10 in the left-right direction increases, the gravity-center-position of the driver may move accordingly. Consequently, there is hardly any time delay between time data of the gravity-center-position GC of the driver and time data of the acceleration CA of the vehicle 10 in the left-right direction. Thus, according to the first embodiment, it is possible to detect a driver's deteriorated physical condition at an early stage before the driver's deteriorated physical condition progresses.

Furthermore, in the first embodiment, the learning value controller 362 regards that the driver's physical condition is normal during a period until a predetermined period elapses after the ignition switch of the vehicle 10 is turned on, and stores an average value of a time delay obtained during the predetermined period in the memory 310 as a learned value. In this way, each time the ignition switch of the vehicle 10 is turned on, a learned value is obtained. Therefore, it is possible to obtain a learned value appropriate for the driver. Thus, according to the first embodiment, it is possible to accurately determine whether the driver's physical condition is good or bad.

Note that in the first embodiment, a time delay in a cross-correlation is compared with a learned value, The embodiment, however, is not limited to the above. For instance, a time delay in a cross-correlation may be compared with a predetermined determination threshold value.

Figure 8:
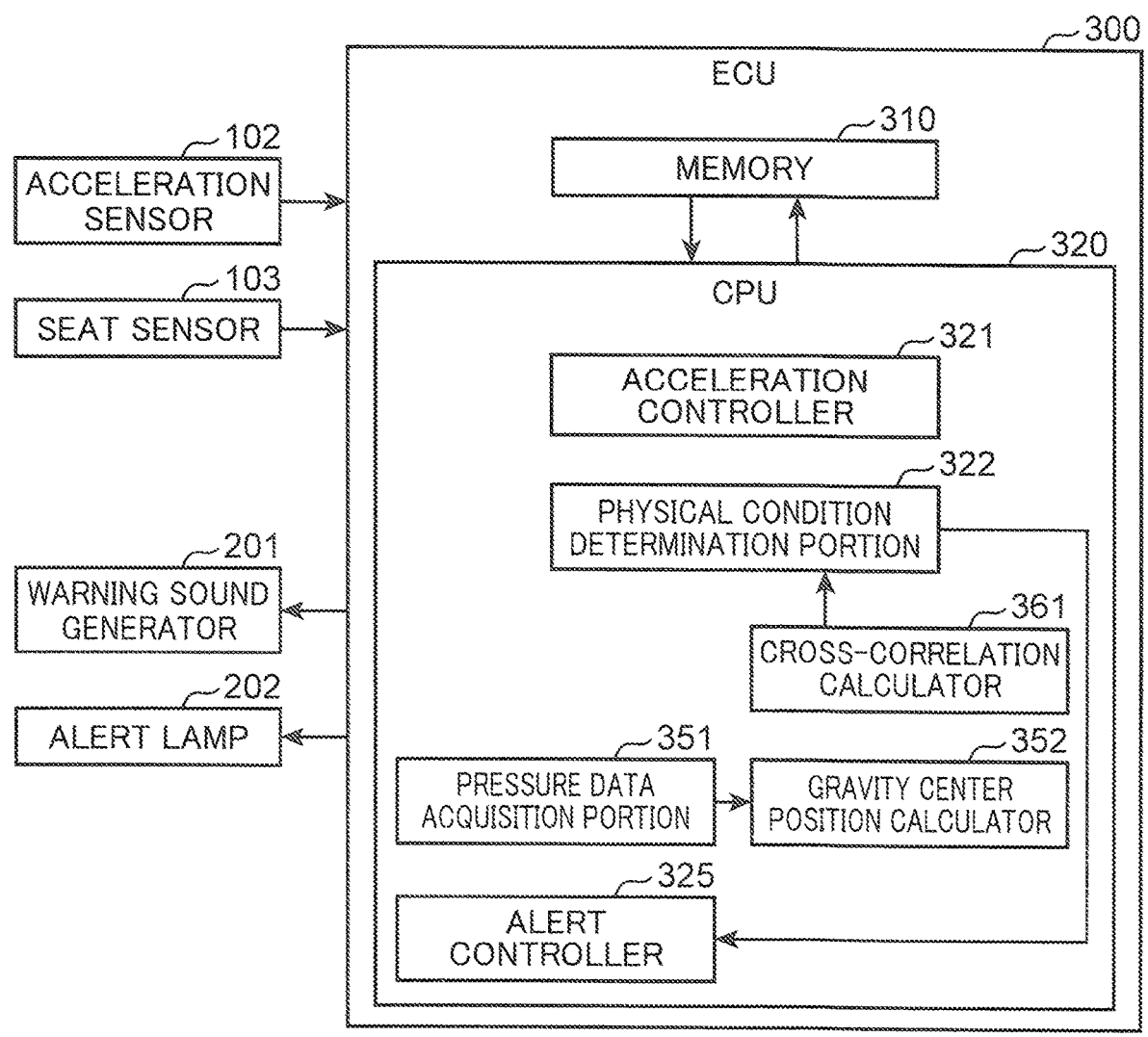
FIG. 8 is a block diagram schematically illustrating another configuration of the vehicle, in which the driver's physical condition of the first embodiment is mounted, which is different from the configuration illustrated in FIG. 1.

FIG. 8 is a block diagram schematically illustrating another configuration of the vehicle, in which the driver's physical condition detection device of the first embodiment is mounted, which is different from the configuration illustrated in FIG. 1. The CPU 320 illustrated in FIG. 8 does not include the learning value controller 362 provided in the CPU 320 illustrated in FIG. 1. The physical condition determination portion 322 in FIG. 8 determines that the driver's physical condition is deteriorated when a time delay in a cross-correlation is not more than a determination threshold value stored in advance in the memory 310. The determination threshold value is determined in advance by an experiment for instance, and is stored in advance in the memory 310. The determination threshold value may be about three seconds, for instance.

Figure 9:
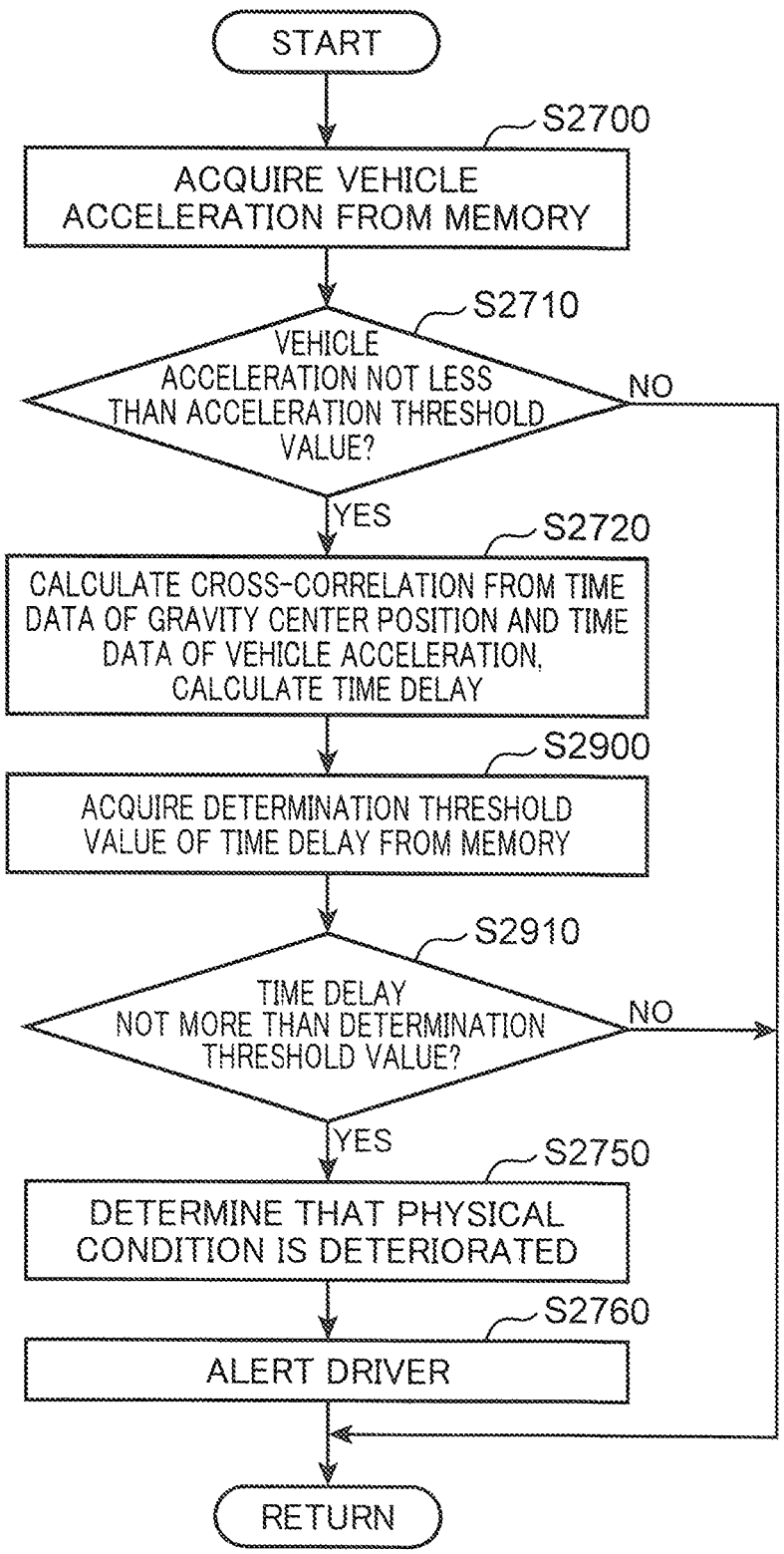
FIG. 9 is a flowchart schematically illustrating an example of a procedure of determining a driver's physical condition in the configuration illustrated in FIG. 8.

FIG. 9 is a flowchart schematically illustrating an example of a procedure of determining a driver's physical condition, in the configuration illustrated in FIG. 8. The flow illustrated in FIG. 9 is executed every predetermined period (e.g. every 100 msec.).

Steps S2700, S2710, and S2720 in FIG. 9 are respectively the same as steps S2700, S2710, and S2720 in FIG. 7. In step S2900 following step S2720, the physical condition determination portion 322 acquires a determination threshold value of a time delay from the memory 310.

In step S2910, the physical condition determination portion 322 determines whether or not a time delay calculated in step S2720 is not more than the determination threshold value. When the calculated time delay is more than the determination threshold, value (NO in step S2910), the process of FIG. 9 is terminated. When the calculated time delay is not more than the determination threshold value (YES in step S2910), the process proceeds to step S2750. Steps S2750 and S2760 are respectively the same as steps S2750 and S2760 in FIG. 7.

As described above, by comparing a time delay in a cross-correlation with a predetermined determination threshold value, it is also possible to detect a deteriorated physical condition of a driver at an early stage before the deteriorated physical condition of the driver progresses.

(Second Embodiment)

Figure 10:
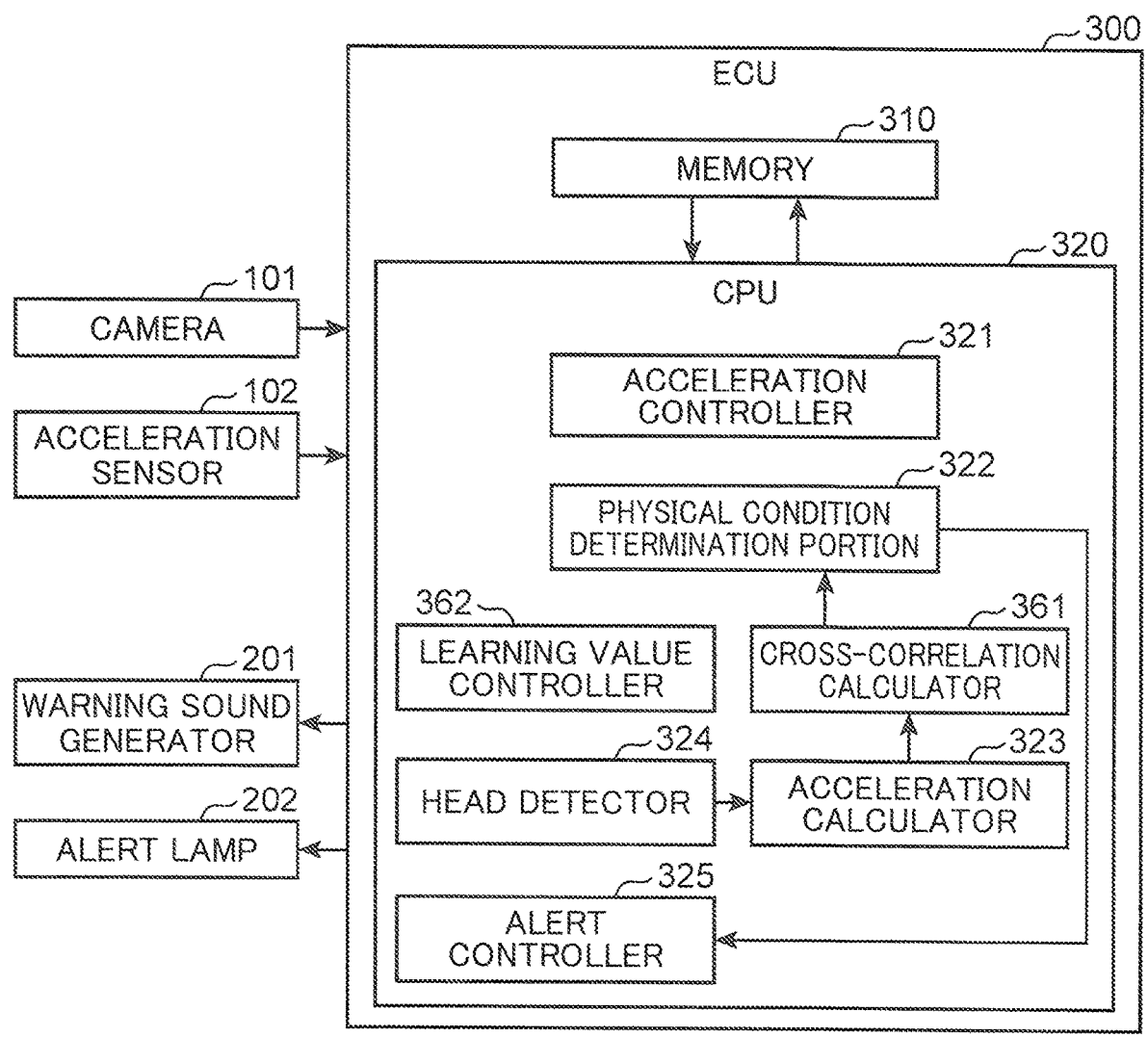
FIG. 10 is a block diagram schematically illustrating a configuration of a vehicle, in which a driver's physical condition detection device of a second embodiment is mounted.

FIG. 10 is a block diagram schematically illustrating a configuration of a vehicle, in which a driver's physical condition detection device of the second embodiment is mounted. In the first embodiment, a driver's physical condition is determined with use of time data of a gravity-center-position of the driver. In the second embodiment, a driver's physical condition is determined with use of time data of an acceleration of a head of the driver.

A vehicle 10 in the second embodiment includes a camera 101, an acceleration sensor 102, a warning sound generator 201, an alert lamp 202, and an electronic control unit (ECU) 300.

The camera 101 (an example of the driver detector) is mounted on a ceiling on the front side of a driver's seat in a passenger compartment of the vehicle 10 for instance, in such a manner that an optical axis of the camera 101 is directed toward the driver's seat in the vehicle 10. The camera 101 captures an image of the driver in the vehicle 10 from the front side to capture an image of a head of the driver which moves in a left-right direction of the vehicle 10. The camera 101 outputs a captured frame image to the ECU 300 every 1/60 sec. for instance. Alternatively, the camera 101 may be mounted on a ceiling above the driver's seat in the passenger compartment of the vehicle 10 in such a manner that an optical axis of the camera 101 is directed toward the driver's seat in the vehicle 10. Further alternatively, a plurality of cameras may be mounted on the ceiling of the passenger compartment of the vehicle 10 in such a manner that an optical axis of each of the cameras is directed toward the driver's seat in the vehicle 10. The camera 101 may be mounted in a passenger compartment of the vehicle 10 in such a manner that motion of the driver's head in the left-right direction of the vehicle 10 can be captured.

In the second embodiment, a CPU 320 functions as an acceleration controller 321, a physical condition determination portion 322, an acceleration calculator 323, a head detector 324, an alert controller 325, a cross-correlation calculator 361, and a learning value controller 362 by being operated in accordance with a program stored in a memory 310.

The head detector 324 detects the driver's head by template matching from a frame image captured by the camera 101, for instance. The head detector 324 stores position coordinates of a center of the driver's head within an imaging area of the camera 101 in the memory 310 for each frame image, for instance. The head detector 324 stores time data of position coordinates of the driver's head for a predetermined period in the memory 310. When the predetermined period is one second for instance, and a frame image is output from the camera 101 every 1/60 sec., sixty pieces of time data of position coordinates of the driver's head are stored in the memory 310.

The acceleration calculator 323 calculates an acceleration of the driver's head in the left-right direction with use of time data of position coordinates of the driver's head, which is stored in the memory 310. For instance, the acceleration calculator 323 calculates a moving distance between frame images from position coordinates of the driver's head for each frame image, and calculates an acceleration from the amount of change of the calculated moving distance for each frame image. The acceleration calculator 323 stores time data of acceleration of the driver's head for a predetermined period in the memory 310. As described above, when the predetermined period is one second. for instance, and a frame image is output from the camera 101 every 1/60 sec., sixty pieces of time data of acceleration of the driver's head are stored in the memory 310.

The physical condition determination portion 322 determines whether or not a driver's physical condition is deteriorated based on judgment as to whether or not there is a time delay of a change in the acceleration of the driver's head in the left-right direction with respect to a change in the acceleration of the vehicle 10 in the left-right direction.

Figure 11:
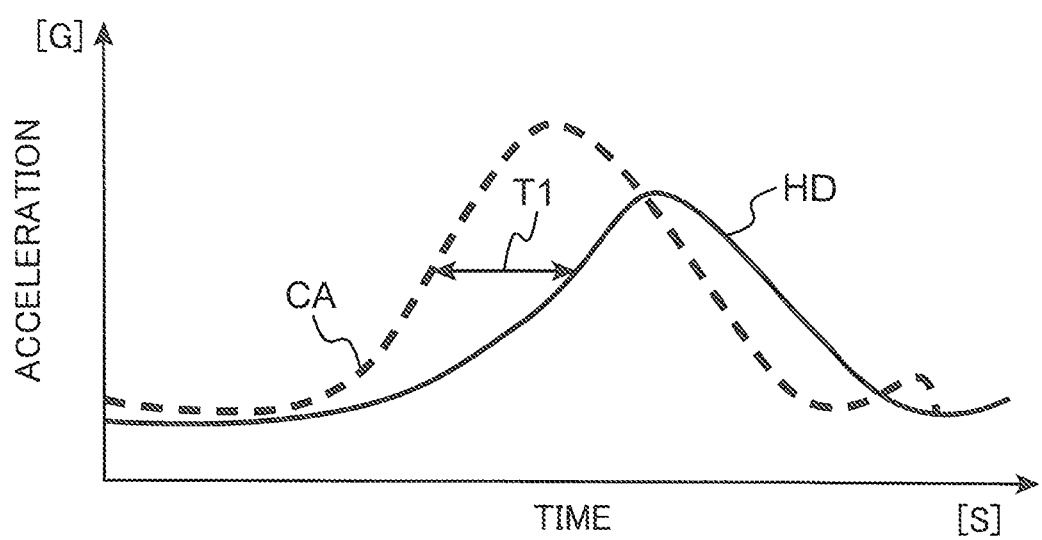
FIG. 11 is a diagram schematically illustrating a change in an acceleration of a vehicle in a left-right direction of the vehicle with time, and a change in an acceleration of a driver's head in the left-right direction with time.
Figure 12:
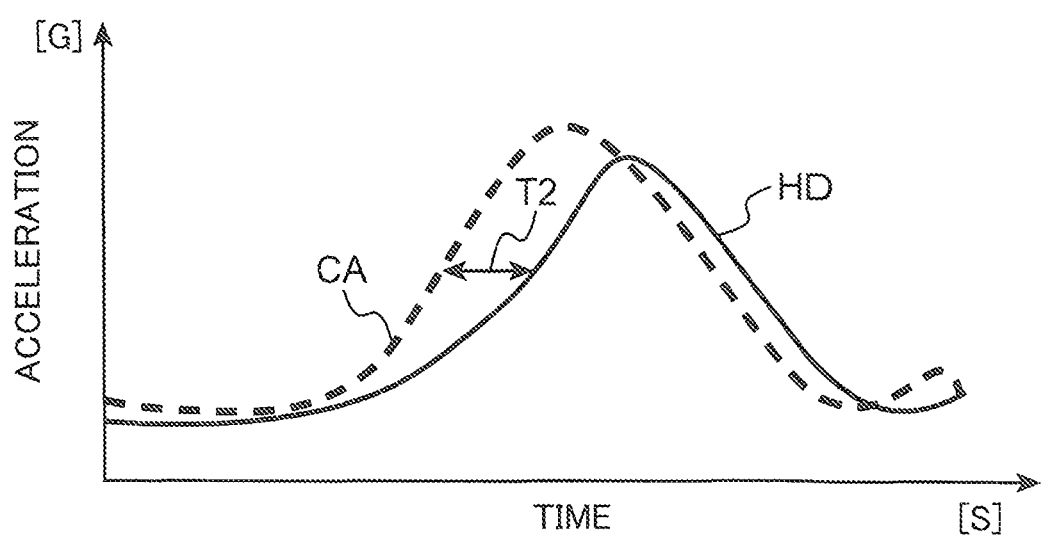
FIG. 12 is a diagram schematically illustrating a change in an acceleration of the vehicle in the left-right direction of the vehicle with time, and a change in an acceleration of the driver's head in the left-right direction with time.

FIG. 11 and FIG. 12 are diagrams schematically illustrating a change in an acceleration CA of the vehicle 10 in the left-right direction with time, and a change in an acceleration HD of the driver's head in the left-right direction with time. FIG. 11 illustrates a case where a driver's physical condition is normal, and FIG. 12 illustrates a case where a driver's physical condition is deteriorated.

When a time delay T1 of a change in the acceleration HD of the driver's head with respect to a change in the acceleration CA of the vehicle in FIG. 11 is compared with a time delay T2 of a change in the acceleration HD of the driver's head with respect to a change in the acceleration CA of the vehicle in FIG. 12, T1>T2.

The reason for this is conceivably as follows. Specifically, when a driver's physical condition is deteriorated, the muscles of the neck are weakened. As a result, the acceleration HD of the driver's head may change as the acceleration CA of the vehicle changes. Consequently, the time delay T2 is relatively small. In other words, the follow-up degree of a change in motion of the driver with respect to a change in motion of the vehicle 10 during driving is high. On the other hand, when the driver's physical condition is normal, the driver tries to tighten the muscles of the neck and tries to resist against a change in the acceleration CA of the vehicle. As a result, the time delay T1 of a change in the acceleration HD of the driver's head is relatively large. In other words, the follow-up degree of a change in motion of the driver with respect to a change in motion of the vehicle 10 during driving is low.

Referring back to FIG. 10, the physical condition determination portion 322 determines whether or not a driver's physical condition is deteriorated only when an acceleration of the vehicle 10 in a left-right direction is not less than a predetermined acceleration threshold value ACth. This is because as far as the acceleration of the vehicle 10 in the left-right direction is small, there is no significant difference in a time delay of a change in the acceleration HD of the driver's head with respect to a change in the acceleration CA of the vehicle between a case where a driver's physical condition is normal and a case where a driver's physical condition is deteriorated. In the embodiment, ACth=0.1 [G], for instance.

The cross-correlation calculator 361 calculates a cross-correlation between time data of an acceleration of the vehicle 10 in the left-right direction, which is stored in the memory 310 by the acceleration controller 321, and time data of an acceleration of the driver's head in the left-right direction, which is stored in the memory 310 by the acceleration calculator 323. As described above, the cross-correlation is obtained by convoluting one of two functions by reversing the order of a signal array with use of a convolution formula of convoluting the two functions. In the embodiment, the two functions are a function representing time data of an acceleration of the vehicle 10 in the left-right direction, and a function representing time data of an acceleration of the driver's head in the left-right direction. The cross-correlation calculator 361 calculates a time delay from an obtained cross-correlation.

Figure 13:
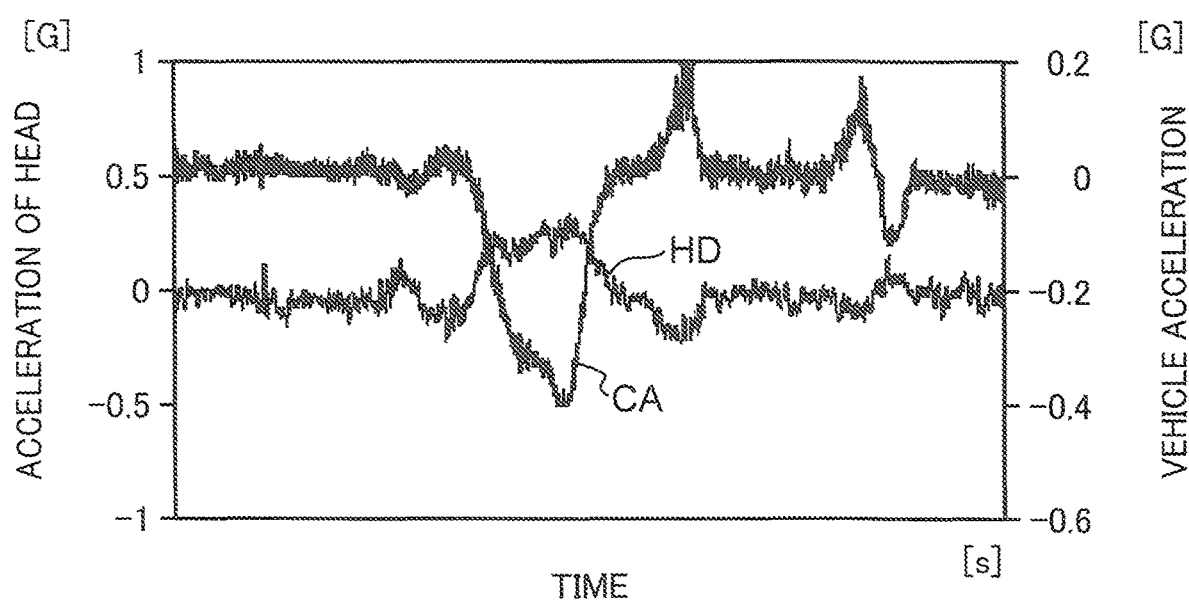
FIG. 13 is a diagram schematically illustrating time data of an acceleration of a vehicle in a left-right direction of the vehicle, and time data of an acceleration of a driver's head in the left-right direction.
Figure 14:
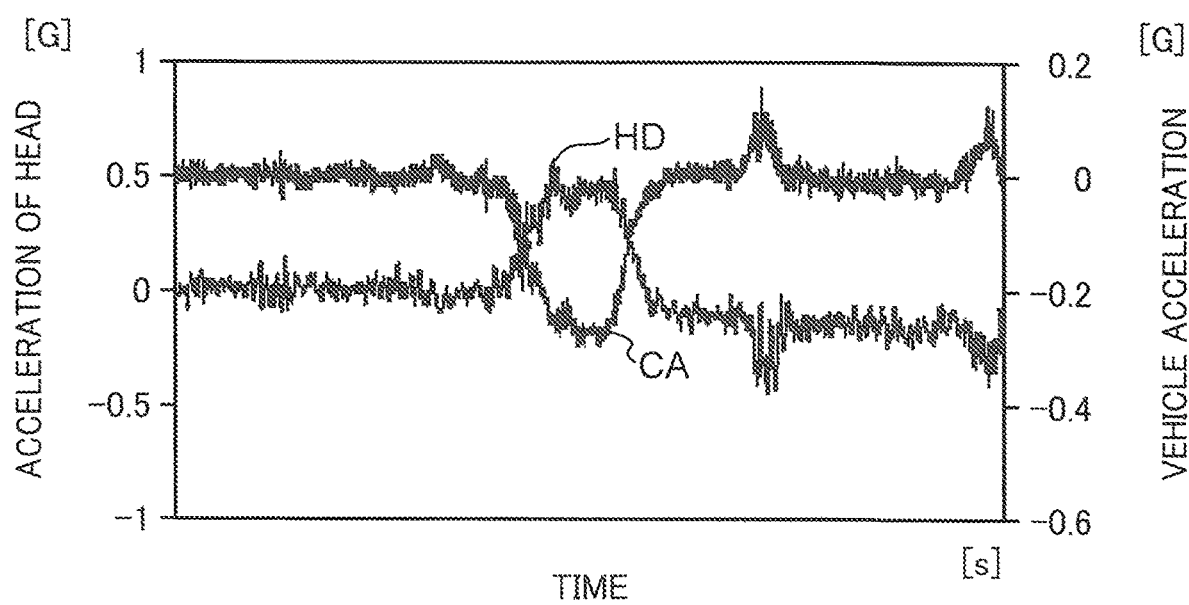
FIG. 14 is a diagram schematically illustrating time data of an acceleration of the vehicle in the left-right direction of the vehicle, and time data of an acceleration of the driver's head in the left-right direction.

FIG. 13 and FIG. 14 are diagrams schematically illustrating time data of the acceleration CA of the vehicle 10 in the left-right direction, and time data of the acceleration HD of the driver's head in the left-right direction. In FIG. 13 and FIG. 14, the horizontal axis denotes a time [second], the left vertical axis denotes an, acceleration [G] of the driver's head, and the right vertical axis denotes an acceleration [G] of the vehicle 10. FIG. 13 illustrates a case where a driver's physical condition is normal, and FIG. 14 illustrates a case where a driver's physical condition is deteriorated.

As illustrated in FIG. 13 and FIG. 14, an acceleration of the vehicle 10 in the left-right direction increases, since the vehicle 10 travelling on a straight road enters a curve. In response to this increase of the acceleration, the acceleration of the driver's head in the left-right direction increases. When a driver's physical condition is normal, as an acceleration of the vehicle 10 in the left-right direction increases, the driver tries to tighten the muscles of the neck and tries to prevent swaying of the head so that the head does not sway due to the increase in the acceleration. Therefore, there is a time delay in a cross-correlation between time data of the acceleration CA of the vehicle 10, and time data of the acceleration HD of the driver's head.

On the other hand, when the driver's physical condition is deteriorated, the acceleration of the driver's head increases. as the acceleration of the vehicle increases, because the muscles of the neck are weakened. As a result, there is hardly any time delay in time data of the acceleration HD of the driver's head with respect to time data of the acceleration CA of the vehicle.

Referring back to FIG. 10, the learning value controller 362 regards that a driver's physical condition is normal during a period until a predetermined period elapses after the ignition switch of the vehicle 10 is turned on, and stores an average value of a time delay in a cross-correlation between time data of the acceleration CA of the vehicle 10 and time data of the acceleration HD of the driver's head, which are obtained for the predetermined period, in the memory 310 as a learned value.

The physical condition determination portion 322 compares a time delay in a cross-correlation between time data of the acceleration CA of the vehicle 10 in the left-right direction and time data of the acceleration HD of the driver's head in the left-right direction, with the learned value stored in the memory 310, and determines whether or not a driver's physical condition is deteriorated based on the comparison result. Specifically, the physical condition determination portion 322 determines that the driver's physical condition is deteriorated, when a time delay in a cross-correlation between time data of the acceleration CA of the vehicle and time data of the acceleration HD of the driver's head is not more than a value K2 times as large as a learned value. The coefficient K2 is a value smaller than 1. In the embodiment, K2=0.5, for instance. The coefficient K2 may be a value equal to the coefficient K1 or may be a value different from the coefficient K1. When the physical condition determination portion 322 determines that the driver's physical condition is deteriorated, the physical condition determination portion 322 notifies the alert controller 325 that the driver's physical condition is deteriorated.

The physical condition determination portion 322 determines whether or not a driver's physical condition is deteriorated only when the acceleration of the vehicle 10 in the left-right direction is not less than the predetermined acceleration threshold value ACth. This is because as far as the acceleration of the vehicle 10 in the left-right direction is small, there is no significant difference in a time delay in a cross-correlation between time data of the acceleration CA and time data of the acceleration HD of the driver's head between a case where a driver's physical condition is normal and a ease where a driver's physical condition is deteriorated. In the embodiment, ACth=0.1 [G], for instance.

The procedure of acquiring an acceleration of the vehicle by the acceleration controller 321 in the second embodiment is the same as the procedure in the first embodiment illustrated in FIG. 5.

Figure 15:
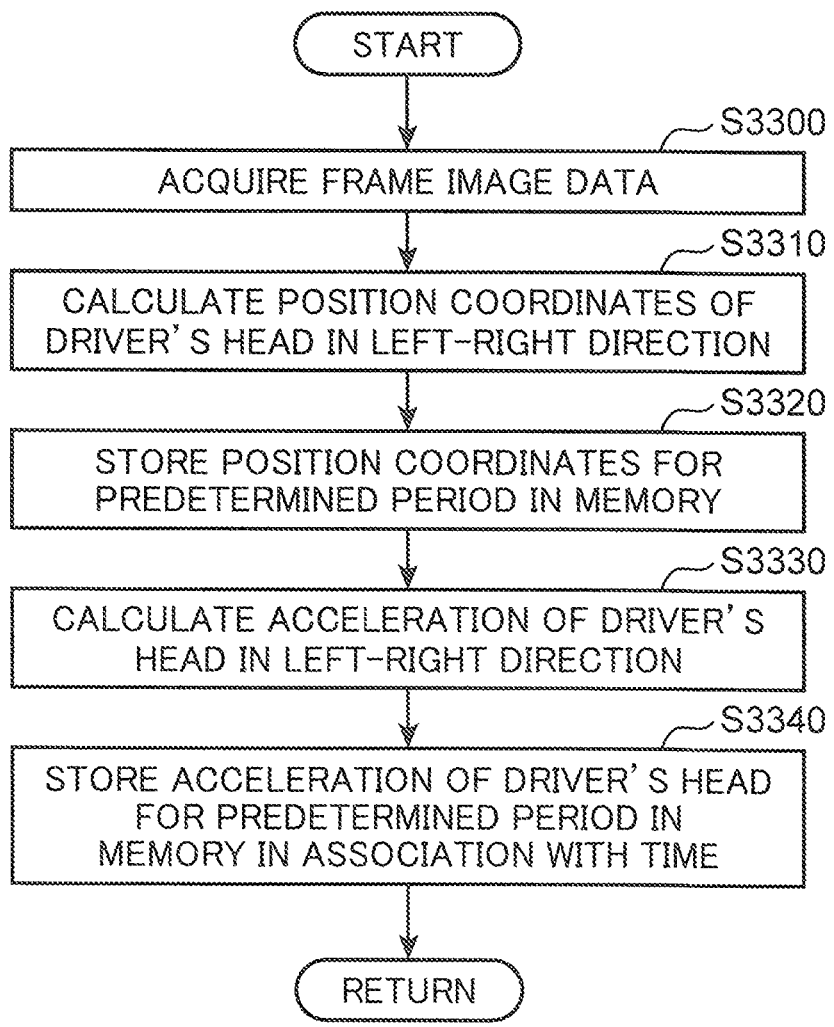
FIG. 15 is a flowchart schematically illustrating an example of a procedure of acquiring an acceleration of a driver's head in the driver's physical condition detection device of the second embodiment.

FIG. 15 is a flowchart schematically illustrating an example of a procedure of acquiring an acceleration of a driver's head in the driver's physical condition detection device of the second embodiment. The flow illustrated in FIG. 15 is executed every predetermined period (e.g. each time a frame image is output from the camera 101, in other words, in the embodiment, every ¹⁄₆₀ sec.).

In step S3300, the head detector 324 acquires data of a frame image captured by the camera 101. In step S3310, the head detector 324 detects a driver's head from the acquired frame image, and calculates position coordinates of a center of the driver's head, for instance. In step S3320, the head detector 324 stores time data of position coordinates of the driver's head for a predetermined period in the memory 310 for each frame image. In other words, the head detector 324 erases oldest position coordinate data from the memory 310 when new position coordinate data is obtained so that position coordinate data for a predetermined period is stored in the memory 310.

In step S3330, the acceleration calculator 323 calculates an acceleration of the driver's head in the left-right direction with use of time data of position coordinates of the driver's head, which is stored in the memory 310. In step S3340, the acceleration calculator 323 stores time data of an acceleration of the driver's head for a predetermined period in the memory 310. As with step S3320, the acceleration calculator 323 erases oldest acceleration data from the memory 310 when new acceleration data is obtained so that acceleration data for a predetermined period is stored in the memory 310. Thereafter, the process of FIG. 15 is terminated.

Figure 16:
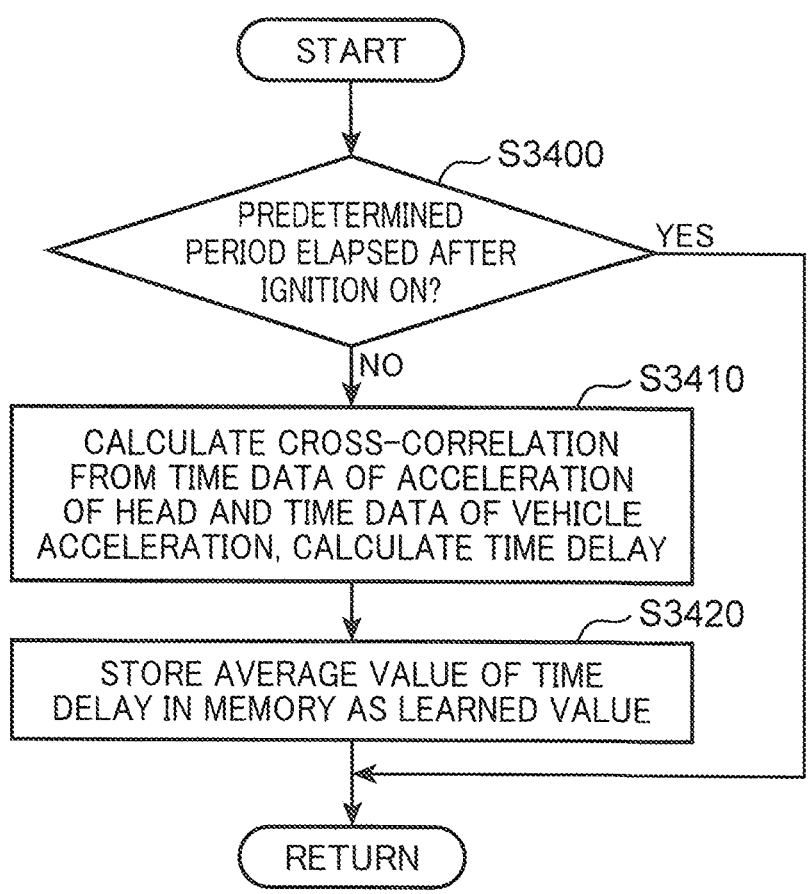
FIG. 16 is a flowchart schematically illustrating an example of a procedure of calculating a learned value of a time delay in the driver's physical condition detection device of the second embodiment.

FIG. 16 is a flowchart schematically illustrating an example of a procedure of calculating a learned value of a time delay in the driver's physical condition detection device of the second embodiment. The flow illustrated in FIG. 16 is executed every predetermined period (e.g. every 100 msec.).

In step S3400, the learning value controller 362 determines whether or not a predetermined period elapses after the ignition switch of the vehicle 10 is turned on.

When a predetermined period does not elapse after the ignition switch of the vehicle 10 is turned on (NO in step S3400), the process proceeds to step S3410. On the other hand, when, a predetermined period elapses after the ignition switch of the vehicle 10 is turned on (YES in step S3400), the process of FIG. 16 is terminated. Specifically, when a judgment result in step S3400 is NO, it is judged that the driver's physical condition is normal, and the process proceeds to step S3410 to perform a process of obtaining a learned value. When a judgment result in step S3400 is YES, the process of FIG. 16 is terminated without performing a process of obtaining a learned value.

In step S3410, the cross-correlation calculator 361 calculates a cross-correlation from time data of an acceleration of the driver's head and time data of an acceleration of the vehicle, which are stored in the memory 310, and calculates a time delay of a peak value of a correlation value. In step S3420, the learning value controller 362 stores an average value of the calculated time delay in the memory 310 as a learned value. Thereafter, the process of FIG. 16 is terminated.

Figure 17:
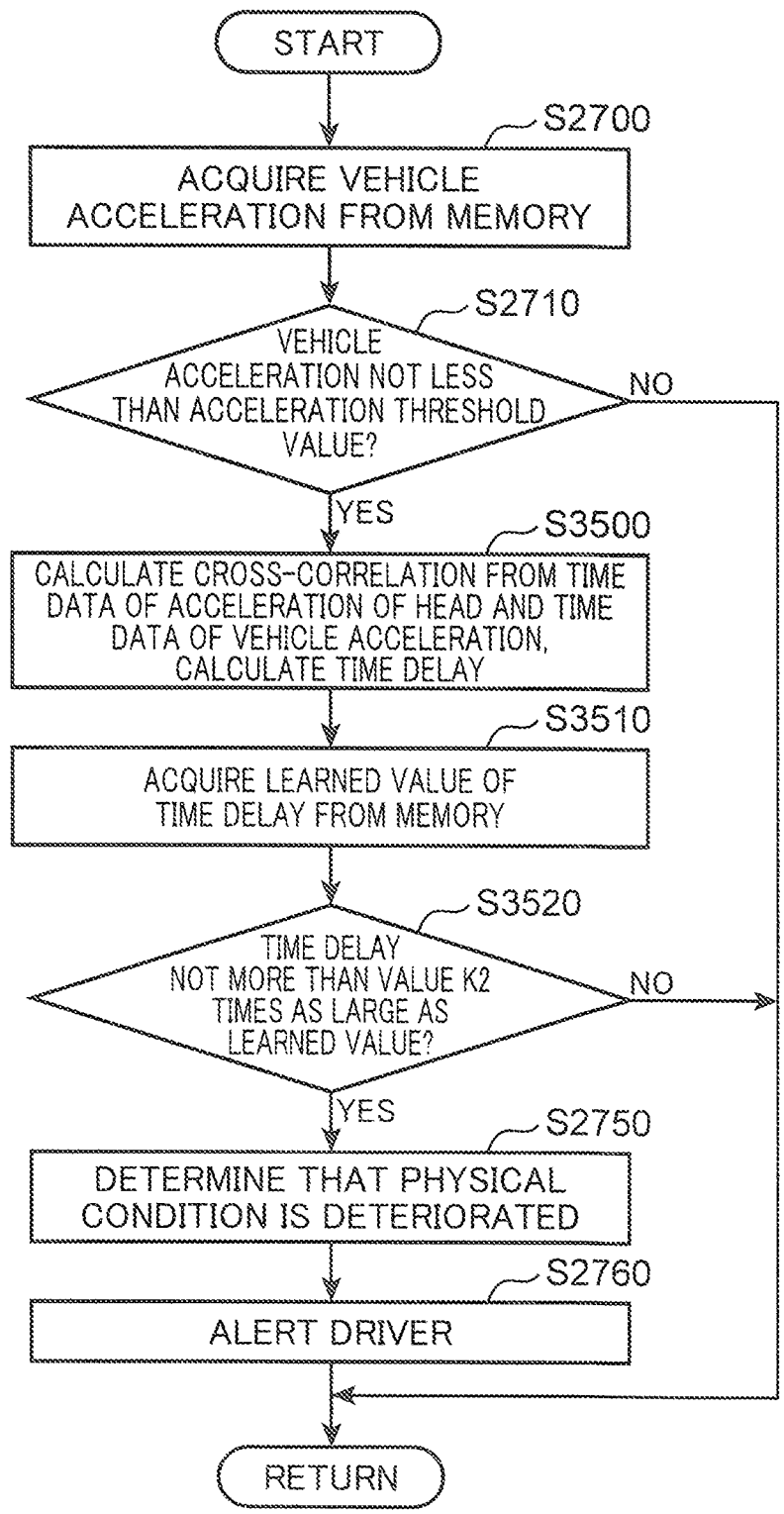
FIG. 17 is a flowchart schematically illustrating an example of a procedure of determining a driver's physical condition in the driver's physical condition detection device of the second embodiment.

FIG. 17 is a flowchart schematically illustrating an example of a procedure of determining a driver's physical condition in the driver's physical condition detection device of the second embodiment. The flow illustrated in FIG. 17 is executed every predetermined period (e.g. every 100 msec.).

Steps S2700 and S2710 are respectively the same as steps S2700 and S2710 in FIG. 7. In step S3500 following step S2710, the cross-correlation calculator 361 calculates across-correlation from time data, of an acceleration of the driver's head, and time data of an acceleration of the vehicle, and calculates a time delay of a peak value of a correlation value. In step S3510, the physical condition determination portion 322 acquires the learned value of the time delay stored in the memory 310, from the memory 310.

In step S3520, the physical condition determination portion 322 determines whether or not a time delay calculated in step S3500 is not more than a value K2 times as large as the learned value acquired in step S3510. When a calculated time delay is more than a value K2 times as large as the learned value (NO in step S3520), the process of FIG. 17 is terminated. When a calculated time delay is not more than a value K2 times as large as the learned value (YES in step S3520), the process proceeds to step S2750. Steps S2750 and S2760 are respectively the same as steps S2750 and S2760 in FIG. 7.

As described above, in the second embodiment, the cross-correlation calculator 361 calculates a cross-correlation from time data of an acceleration of the driver's head, and time data of an acceleration of the vehicle, and calculates a time delay of a peak value of a correlation value. The physical condition determination portion 322 determines that the driver's physical condition is deteriorated when a time delay is not more than a value K2 times as large as a learned value. When a driver's physical condition is deteriorated, the muscles of the neck or the upper body may be weakened due to slight lowering of the consciousness, and it may be difficult for the driver to tighten the muscles of the upper body. Therefore, as an acceleration of the vehicle 10 in the left-right direction increases, an acceleration of the driver's head may also increase. As a result, there is hardly any time delay between time data of the acceleration CA of the vehicle, and time data of the acceleration HD of the driver's head. Thus, according to the second embodiment, it is possible to detect a driver's deteriorated physical condition at an early stage before the driver's deteriorated physical condition progresses.

Further, in the second embodiment, as with the first embodiment, the learning value controller 362 regards that the driver's physical condition is normal during a period until a predetermined period elapses after the ignition switch of the vehicle 10 is turned on, and stores an average value of a time delay obtained during the predetermined period in the memory 310 as a learned value. In this way, each time the ignition switch of the vehicle 10 is turned on, a learned value is obtained. Therefore, it is possible to obtain a learned value appropriate for the driver. Thus, according to the second embodiment, as with the first embodiment, it is possible to accurately determine whether the driver's physical condition is good or bad.

Note that in the second embodiment, a time delay in a cross-correlation is compared with a learned value. The embodiment, however, is not limited to the above. For instance, a time delay in a cross-correlation may be compared with a predetermined determination threshold value.

Figure 18:
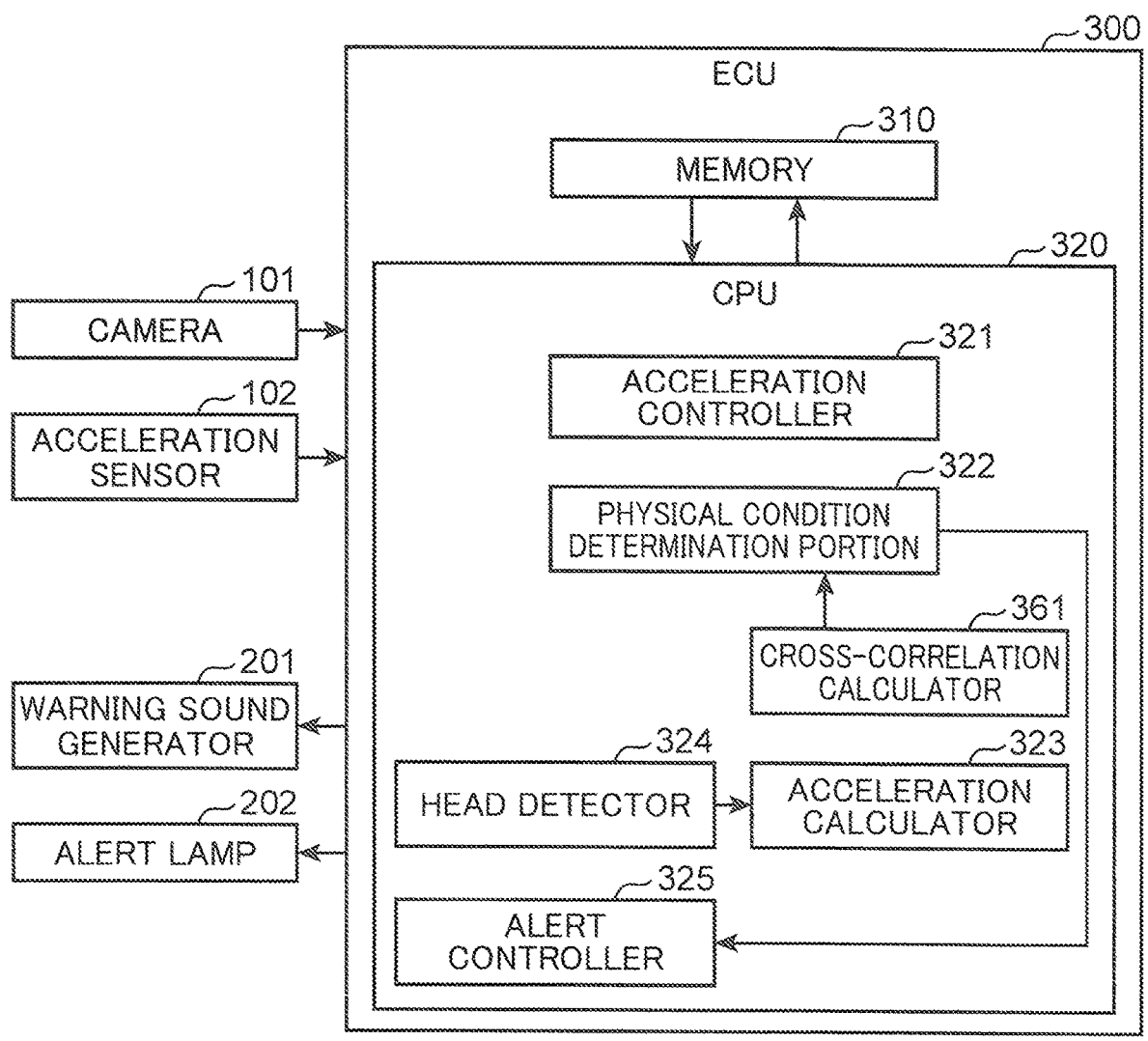
FIG. 18 is a block diagram schematically illustrating another configuration of the vehicle, in which the driver's physical condition detection device of the second embodiment is mounted, which is different from the configuration illustrated in FIG. 10.

FIG. 18 is a block diagram schematically illustrating another configuration of the vehicle, in which the driver's physical condition detection device of the second embodiment is mounted, which is different from the configuration illustrated in FIG. 10. A CPU 320 illustrated in FIG. 18 does not include the learning value controller 362 provided in the CPU 320 illustrated in FIG. 10. A physical condition determination portion 322 in FIG. 18 determines that the driver's physical condition is deteriorated when a time delay in a cross-correlation is not more than a determination threshold value stored in advance in a memory 310. The determination threshold value is determined in advance by an experiment for instance, and is stored in advance in the memory 310. The determination threshold value may be about three seconds, for instance.

Figure 19:
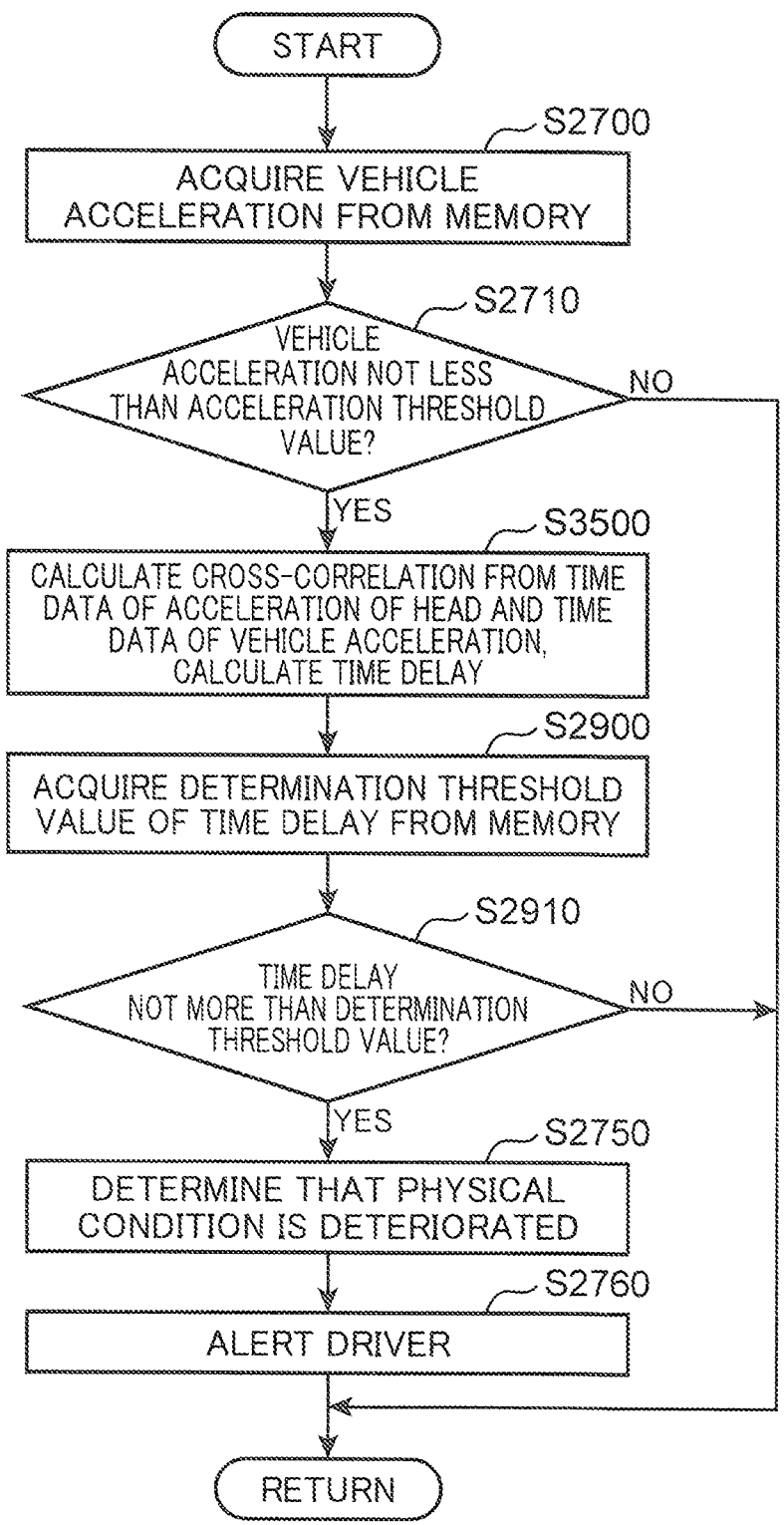
FIG. 19 is a flowchart schematically illustrating an example of a procedure of determining a driver's physical condition in the configuration illustrated in FIG. 18.

FIG. 19 is a flowchart schematically illustrating an example of a procedure of determining a driver's physical condition in the configuration illustrated in FIG. 18. The flow illustrated in FIG. 19 is executed every predetermined period (e.g. every 100 msec.).

Steps S2700 and S2710 in FIG. 19 are respectively the same as steps S2700 and S2710 in FIG. 7. Step S3500 in FIG. 19 is the same as step S3500 in FIG. 17. Steps S2900 and S2910 in FIG. 19 are respectively the same as steps S2900 and S2910 in FIG. 9. Steps S2750 and S2760 in FIG. 19 are respectively the same as steps S2750 and S2760 in FIG. 7.

As described above, by comparing a time delay in a cross-correlation with a predetermined determination threshold value, it is possible to detect a driver's deteriorated physical condition at an early stage before the driver's deteriorated physical condition progresses as with the above second embodiment.

Note that the aforementioned specific embodiments mainly include the invention having the following configuration.

An aspect of the technique disclosed herein is directed to a driver's physical condition detection device for detecting a physical condition of a driver driving a vehicle. The driver's physical condition, detection device includes: a vehicle detector configured to detect a change in motion of the vehicle during driving; a driver detector configured to detect a change in motion of the driver; a calculator configured to calculate a follow-up degree of the change in motion of the driver with respect to the change in motion of the vehicle during driving; and a physical condition determination portion configured to perform a determination process of determining whether or not the physical condition of the driver is deteriorated, based on the follow-up degree.

According to the aforementioned configuration, the calculator calculates the follow-up degree of the change in motion of the driver with respect to the change in motion of the vehicle during driving. The physical condition determination portion performs the determination process of determining whether or not the driver's physical condition is deteriorated based on the follow-up degree. The follow-up degree of the change in motion of the driver with respect to the change in motion of the vehicle during driving is different between a case where the driver's physical condition is normal, and a stage when the driver's physical condition starts to deteriorate, because in the stage when the driver's physical condition starts to deteriorate, the muscles of the neck or the upper body are weakened. According to the aforementioned configuration, it is possible to detect a driver's deteriorated physical condition at an early stage before the driver's deteriorated physical condition progresses.

In the aforementioned configuration, for instance, the vehicle detector may detect a change in motion of the vehicle in a left-right direction of the vehicle as the change in motion of the vehicle during driving. The driver detector may detect a change in motion of the driver in the left-right direction as the change in motion of the driver. The calculator may calculate a follow-up degree of the change in motion of the driver in the left-right direction with respect to the change in motion of the vehicle in the left-right direction during driving, as the follow-up degree.

According to the aforementioned configuration, the follow-up degree of the change in motion of the driver in the left-right direction with respect to the change in motion of the vehicle in the left-right direction during driving is calculated. The follow-up degree of the change in motion of the driver in the left-right direction with respect to the change in motion of the vehicle in the left-right direction during driving is significantly different between a case where the driver's physical condition is normal, and a stage when the driver's physical condition starts to deteriorate, as compared with a case of the front-rear direction of the vehicle. According to the aforementioned configuration, it is possible to detect a driver's deteriorated physical condition at an early stage before the driver's deteriorated physical condition progresses.

In the aforementioned configuration, for instance, the driver detector may detect a change in a gravity-center-position of the driver, as the change in motion of the driver. The calculator may calculate a follow-up degree of the change in the gravity-center-position of the driver with respect to the change in motion of the vehicle during driving.

According to the aforementioned configuration, the driver detector detects the change in the gravity-center-position of the driver, as the change in motion of the driver. The calculator calculates the follow-up degree of the change in the gravity-center-position of the driver with respect to the change in motion of the vehicle during driving. The follow-up degree of the change in the gravity-center-position of the driver with respect to the change in motion of the vehicle during driving is different between a case where the driver's physical condition is normal, and a stage when the driver's physical condition starts to deteriorate, because in the stage when the driver's physical condition starts to deteriorate, the muscles of the neck or the upper body are weakened. According to the aforementioned configuration, it is possible to detect a driver's deteriorated physical condition at an early stage before the driver's deteriorated physical condition progresses.

In the aforementioned configuration, for instance, the driver detector may detect an acceleration of a head of the driver, as the change in motion of the driver. The calculator may calculate a follow-up degree of the acceleration of the head of the driver with respect to the change in motion of the vehicle during driving, as the follow-up degree.

According to the aforementioned configuration, the driver detector detects the acceleration of the head of the driver, as the change in motion of the driver. The calculator calculates the follow-up degree of the acceleration of the head of the driver with respect to the change in motion of the vehicle during driving, as the follow-up degree. The follow-up degree of the acceleration of the head of the driver with respect to the change in motion of the vehicle during driving is different between a case where the driver's physical condition is normal, and a stage when the driver's physical condition starts to deteriorate, because in the stage when the driver's physical condition starts to deteriorate, the muscles of the neck or the upper body are weakened. According to the aforementioned configuration, it is possible to detect a driver's deteriorated physical condition at an early stage before the driver's deteriorated physical condition progresses.

In the aforementioned configuration, for instance, the calculator may calculate a time delay of the change in motion of the driver with respect to the change in motion of the vehicle during driving, as the follow-up degree. The physical condition determination portion may determine that the physical condition of the driver is deteriorated when the time delay is not more than a reference period.

According to the aforementioned configuration, the calculator calculates the time delay of the change in motion of the driver with respect to the change in motion of the vehicle during driving, as the follow-up degree. The physical condition determination portion determines that the physical condition of the driver is deteriorated when the time delay is not more than the reference period. When, the muscles of the neck or the upper body are weakened in the stage when the driver's physical condition starts to deteriorate, the time delay of the change in motion of the driver with respect to the change in motion of the vehicle during driving becomes small. According to the aforementioned configuration, it is possible to detect a driver's deteriorated physical condition at an early stage before the driver's deteriorated physical condition progresses.

In the aforementioned configuration, for instance, the calculator may calculate a cross-correlation between time data of the change in motion of the vehicle during driving and time data of the change in motion of the driver to calculate the time delay.

According to the aforementioned configuration, the calculator calculates the cross-correlation between time data of the change in motion of the vehicle during driving, and time data of the change in motion of the driver to calculate the time delay. According to the aforementioned configuration, it is possible to accurately calculate the time delay.

In the aforementioned configuration, for instance, the physical condition determination portion may perform the determination process only when a magnitude of the change in motion of the vehicle during driving is not less than a predetermined threshold value.

According to the aforementioned configuration, the physical condition determination portion performs the determination process only when the magnitude of the change in motion of the vehicle during driving is not less than the predetermined threshold value. When the magnitude of the change in motion of the vehicle during driving is less than the predetermined threshold value, there may be no significant difference in the follow-up degree of the change in motion of the driver with respect to the change in motion of the vehicle during driving between a case where the driver's physical condition is normal and a case where the driver's physical condition is deteriorated. According, to the aforementioned configuration, it is possible to accurately determine whether or not the driver's physical condition is deteriorated.

In the aforementioned configuration, for instance, the vehicle detector may include an acceleration sensor configured to detect an acceleration of the vehicle, as the change in motion of the vehicle during driving.

According to the aforementioned configuration, the acceleration sensor detects the acceleration of the vehicle, as the change in motion of the vehicle during driving. The physical condition determination portion performs the determination process, based on the follow-up degree of the change in Motion of the driver with respect to the acceleration of the vehicle. The follow-up degree of the change in motion of the driver with respect to the acceleration of the vehicle is different between a case where the driver's physical condition is normal, and a stage when the driver's physical condition starts to deteriorate. According to the aforementioned configuration, it is possible to detect a driver's deteriorated physical condition at an early stage before the driver's deteriorated physical condition progresses.

Another aspect of the technique disclosed herein is directed to a driver's physical condition detection method for use in a driver's physical condition detection device for detecting a physical condition of a driver driving a vehicle. The driver's physical, condition detection method includes; a vehicle detecting step of detecting a change in motion of the vehicle during driving; a driver detecting step of detecting a change in motion of the driver; a calculating step of calculating a follow-up degree of the change in motion of the driver with respect to the change in motion of the vehicle during driving; and a physical condition determining step of performing a determination process of determining whether or not the physical condition of the driver is deteriorated, based on the follow-up degree.

According to the aforementioned configuration, in the calculating step, the follow-up degree of the change in motion of the driver with respect to the change in motion of the vehicle during driving is calculated. In the physical condition determining step, the determination process of determining whether or not the driver's physical condition is deteriorated is performed, based on the follow-up degree. The follow-up degree of the change in motion of the driver with respect to the change in motion of the vehicle during driving is different between a case where the driver's physical condition is normal, and a stage when the driver's physical condition starts to deteriorate, because the muscles of the neck or the upper head are weakened in the stage when the driver's physical condition starts to deteriorate. According to the aforementioned configuration, it is possible to detect a driver's deteriorated physical condition at an early stage before the driver's deteriorated physical condition progresses.

This application claims the benefit of priority to Japanese Patent Application No. 2016-166124 filed on Aug. 26, 2016, the entire content of which is hereby incorporated herein by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should he construed as being included therein.

The invention claimed is:

1. A driver's physical condition detection device for detecting a physical condition of a driver driving a vehicle, comprising:
   a vehicle detector configured to detect a change in motion of the vehicle during driving;
   a driver detector configured to detect a change in motion of the driver;
   a degree calculator configured to calculate a follow-up degree of the change in motion of the driver with respect to the change in motion of the vehicle during driving; and
   a physical condition determination portion configured to perform a determination process of determining whether or not the physical condition of the driver is deteriorated, based on the follow-up degree,
   wherein the driver detector includes:
     a camera configured to capture an image of the driver in the vehicle;
     a head detector configured to detect a head of the driver from an image captured by the camera; and
     an acceleration calculator configured to calculate an acceleration of the head of the driver in a left-right direction of the vehicle, as the change in motion of the driver,
   wherein the vehicle detector detects an acceleration of the vehicle in the left-right direction, as the change in motion of the vehicle during driving,
   wherein the degree calculator calculates a time delay of the acceleration of the head of the driver with respect to the acceleration of the vehicle during driving, as the follow-up degree, and
   wherein the physical condition determination portion determines that the physical condition of the driver is deteriorated when the time delay is not more than a reference period.

2. The driver's physical condition detection device according to claim 1, wherein
   the degree calculator calculates a cross-correlation between time data of the acceleration of the vehicle during driving and time data of the acceleration of the head of the driver to calculate the time delay.

3. The driver's physical condition detection device according to claim 1, wherein
   the physical condition determination portion performs the determination process only when a magnitude of the acceleration of the vehicle during driving is not less than a predetermined threshold value.

4. A driver's physical condition detection method for use in a driver's physical condition detection device for detecting a physical condition of a driver driving a vehicle, comprising:
   a vehicle detecting step of detecting a change in motion of the vehicle during driving;
   a driver detecting step of detecting a change in motion of the driver;
   a degree calculating step of calculating a follow-up degree of the change in motion of the driver with respect to the change in motion of the vehicle during driving; and
   a physical condition determining step of performing a determination process of determining whether or not the physical condition of the driver is deteriorated, based on the follow-up degree, wherein
   the driver detecting step includes:
     an image capturing step of capturing an image of the driver in the vehicle using a camera;
     a head detecting step of detecting a head of the driver from an image captured in the image capturing step; and
     an acceleration calculating step of calculating an acceleration of the head of the driver in a left-right direction of the vehicle, as the change in motion of the driver,
   the vehicle detecting step detects an acceleration of the vehicle in the left-right direction, as the change in motion of the vehicle during driving,
   the degree calculating step calculates a time delay of the acceleration of the head of the driver with respect to the acceleration of the vehicle during driving, as the follow-up degree, and
   the physical condition determining step determines that the physical condition of the driver is deteriorated when the time delay is not more than a reference period.

* * * * *